US011889272B2

(12) United States Patent
Bervoets et al.

(10) Patent No.: US 11,889,272 B2
(45) Date of Patent: Jan. 30, 2024

(54) IMPLANTABLE MEDICAL DEVICE

(71) Applicant: Cochlear Limited, Macquarie University (AU)

(72) Inventors: Wim Bervoets, Wilrijk (BE); Patrik Kennes, Herent (BE); Bart Carpentier, Mechelen (BE); Marcus Andersson, Mölnlycke (SE)

(73) Assignee: Cochlear Limited, Macquarie University (AU)

( * ) Notice: Subject to any disclaimer, the term of this patent is extended or adjusted under 35 U.S.C. 154(b) by 1137 days.

(21) Appl. No.: 16/430,278

(22) Filed: Jun. 3, 2019

(65) Prior Publication Data

US 2019/0289412 A1 Sep. 19, 2019

Related U.S. Application Data

(62) Division of application No. 13/271,909, filed on Oct. 12, 2011, now abandoned.

(51) Int. Cl.
*H04R 25/00* (2006.01)
*A61F 2/18* (2006.01)

(52) U.S. Cl.
CPC ...... *H04R 25/606* (2013.01); *A61F 2002/183* (2013.01); *H04R 2460/13* (2013.01)

(58) Field of Classification Search
CPC .... H04R 25/60; H04R 25/602; H04R 25/603; H04R 25/604; H04R 25/606; H04R 25/609; H04R 2460/13
See application file for complete search history.

(56) References Cited

U.S. PATENT DOCUMENTS

| 2,487,038 A | 11/1949 | Baum |
| 2,641,328 A | 6/1953 | Beaudry |
| 3,768,977 A | 10/1973 | Brumfield et al. |
| 4,055,233 A | 10/1977 | Huntress |
| 4,333,469 A | 6/1982 | Jeffcoat et al. |
| 4,488,561 A | 12/1984 | Doring |
| 4,532,930 A | 8/1985 | Crosby et al. |
| 4,590,946 A | 5/1986 | Loeb |
| 4,612,915 A | 9/1986 | Hough et al. |
| 4,744,792 A | 5/1988 | Sander et al. |
| 4,904,233 A | 2/1990 | Hakansson et al. |
| 4,986,831 A | 1/1991 | King et al. |
| 5,176,620 A | 1/1993 | Gilman |
| 5,277,694 A | 1/1994 | Leysieffer et al. |

(Continued)

FOREIGN PATENT DOCUMENTS

KR 20-0401424 Y1 11/2005
RU 2282426 C1 8/2006
(Continued)

OTHER PUBLICATIONS

Gerald A. Niznick, "Achieving Osseointegration in Soft Bone: The Search for Improved Results," Oral Health, Aug. 2000, pp. 27-32.
(Continued)

*Primary Examiner* — Carrie R Dorna
(74) *Attorney, Agent, or Firm* — Pilloff Passino & Cosenza LLP; Martin J. Cosenza

(57) ABSTRACT

An implant configured for secured implantation into a recess formed in a recipient's bone and to removably retain a separate component in a compartment thereof such that the separate component is removable from the implant without removing the implant from the bone.

26 Claims, 15 Drawing Sheets

(56) References Cited

U.S. PATENT DOCUMENTS

| | | |
|---|---|---|
| 5,282,253 A | 1/1994 | Konomi |
| 5,443,493 A | 8/1995 | Byers et al. |
| 5,558,618 A | 9/1996 | Maniglia |
| 5,572,594 A | 11/1996 | Devoe et al. |
| 5,738,521 A | 4/1998 | Dugot |
| 5,814,095 A | 9/1998 | Muller et al. |
| 5,881,158 A | 3/1999 | Lesinski et al. |
| 5,906,635 A | 5/1999 | Maniglia |
| 5,999,632 A | 12/1999 | Leysieffer et al. |
| 6,042,380 A | 3/2000 | De Rowe |
| 6,070,105 A | 5/2000 | Kuzma |
| 6,125,302 A | 9/2000 | Kuzma |
| 6,132,384 A | 10/2000 | Christopherson et al. |
| 6,161,046 A | 12/2000 | Maniglia et al. |
| 6,293,903 B1 | 9/2001 | Kasic et al. |
| 6,381,336 B1 | 4/2002 | Lesinski et al. |
| 6,427,086 B1 | 7/2002 | Fischell et al. |
| 6,516,228 B1 | 2/2003 | Berrang et al. |
| 6,537,200 B2 | 3/2003 | Leysieffer et al. |
| 6,565,503 B2 | 5/2003 | Leysieffer et al. |
| 6,575,894 B2 | 6/2003 | Leysieffer et al. |
| 6,618,623 B1 | 9/2003 | Pless et al. |
| 6,697,674 B2 | 2/2004 | Leysieffer |
| 6,730,015 B2 | 5/2004 | Schugt et al. |
| 6,840,919 B1 | 1/2005 | Hakansson |
| 7,043,040 B2 | 5/2006 | Westerkull |
| 7,346,391 B1 | 3/2008 | Osorio et al. |
| 7,937,156 B2 | 5/2011 | Gibson |
| 7,974,700 B1 | 7/2011 | Gibson |
| 9,545,522 B2 | 1/2017 | Gibson et al. |
| 10,610,691 B2 | 4/2020 | Gibson et al. |
| 2002/0019669 A1 | 2/2002 | Berrang et al. |
| 2002/0091419 A1 | 7/2002 | Firlik et al. |
| 2002/0138115 A1 | 9/2002 | Baumann |
| 2004/0032962 A1 | 2/2004 | Westerkull |
| 2004/0260361 A1 | 12/2004 | Gibson |
| 2006/0030852 A1 | 2/2006 | Sevrain |
| 2006/0050913 A1 | 3/2006 | Westerkull |
| 2006/0116743 A1 | 6/2006 | Gibson et al. |
| 2007/0191673 A1 | 8/2007 | Ball et al. |
| 2009/0087009 A1 | 4/2009 | van Halteren et al. |
| 2009/0099658 A1 | 4/2009 | Dalton et al. |
| 2009/0141919 A1 | 6/2009 | Spitaels et al. |
| 2009/0209806 A1 | 8/2009 | Hakansson |
| 2010/0145135 A1 | 6/2010 | Ball et al. |
| 2010/0145162 A1 | 6/2010 | Devauchelle et al. |
| 2011/0160855 A1 | 6/2011 | Gibson |
| 2011/0208303 A1 | 8/2011 | Gibson |
| 2011/0264170 A1 | 10/2011 | Gibson |
| 2013/0096366 A1 | 4/2013 | Bervoets et al. |
| 2018/0169416 A1 | 6/2018 | Gibson et al. |

FOREIGN PATENT DOCUMENTS

| | | |
|---|---|---|
| WO | 8300999 A1 | 3/1983 |
| WO | 9429932 A1 | 12/1994 |
| WO | 9705673 A1 | 2/1997 |
| WO | 9736457 A1 | 10/1997 |
| WO | 9906108 A1 | 2/1999 |
| WO | 0071063 A1 | 11/2000 |
| WO | 0110369 A1 | 2/2001 |
| WO | 03070133 A1 | 8/2003 |
| WO | 03092326 A1 | 11/2003 |
| WO | 2004014269 A1 | 2/2004 |
| WO | 2004014270 A1 | 2/2004 |
| WO | 2007053882 A1 | 5/2007 |
| WO | 2009099658 A2 | 8/2009 |
| WO | 2010089420 A2 | 8/2010 |
| WO | 2011017733 A1 | 2/2011 |

OTHER PUBLICATIONS

"Passive." Merriam-Webster.com. 2015. http://www.merriam-webster.com/dictionary/passive. Accessed Jan. 9, 2015.

"Active." Merriam-Webster.com. 2015. http://www.merriam-webster.com/dictionary/active. Accessed Jan. 9, 2015.

"Retain." Merriam-Webster.com. 2015. http://www.merriam-webster.com/dictionary/retain. Accessed Jan. 9, 2015.

International Search Report and Written Opinion for International Application No. PCT/IB2012/055565 dated Feb. 27, 2013.

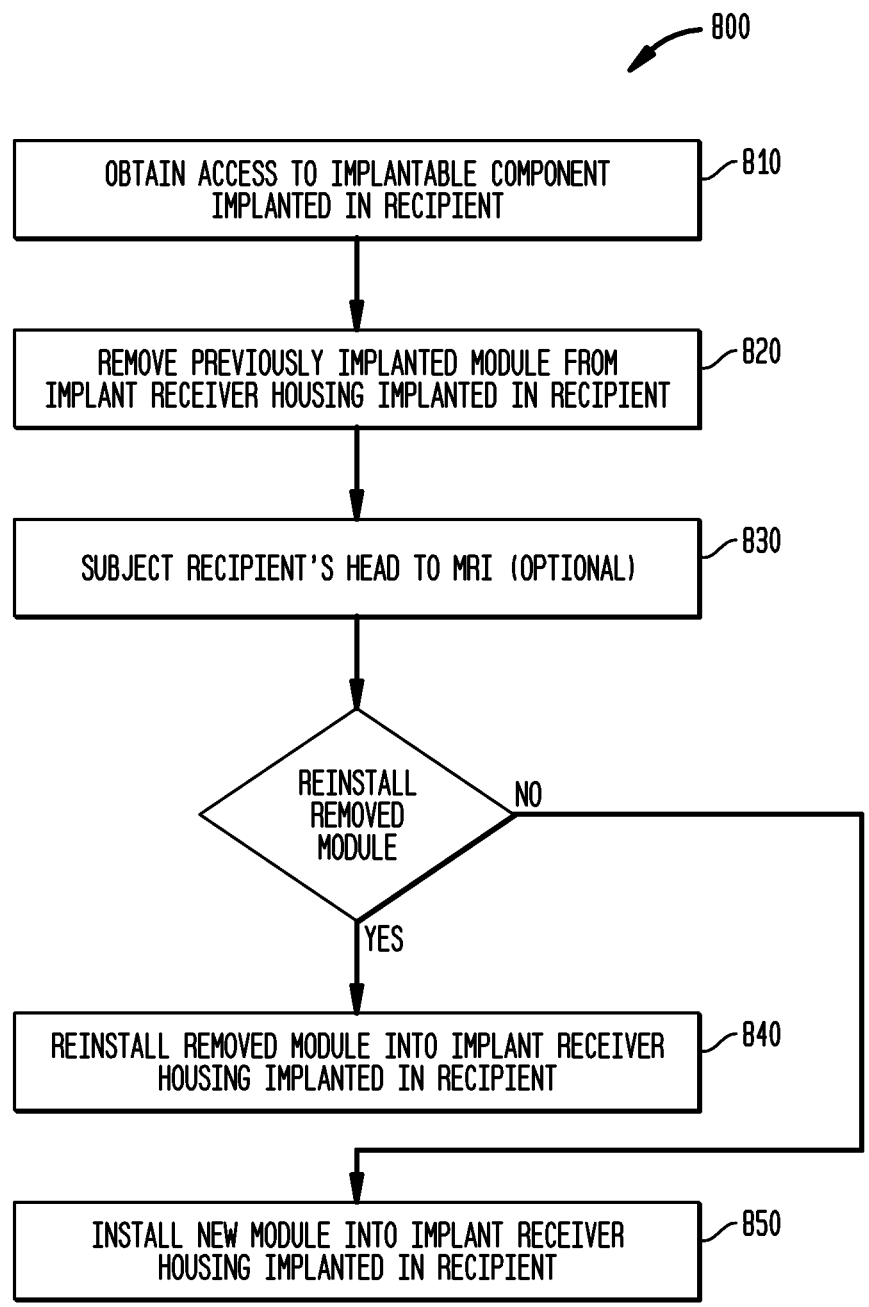

IMPLANTABLE MEDICAL DEVICE

The present application is a Divisional Application of U.S. patent application Ser. No. 13/271,909, filed Oct. 12, 2011, naming Wim BERVOETS as an inventor. The entire contents of this application are incorporated herein by reference in its entirety.

BACKGROUND

Field of the Invention

The present invention relates generally to implantable medical devices.

Related Art

Hearing loss, which may be due to many different causes, is generally of two types: conductive and sensorineural. Sensorineural hearing loss is due to the absence or destruction of the hair cells in the cochlea that transduce sound signals into nerve impulses. Various hearing prostheses are commercially available to provide individuals suffering from sensorineural hearing loss with the ability to perceive sound. For example, cochlear implants use an electrode array implanted in the cochlea of a recipient to bypass the mechanisms of the ear. More specifically, an electrical stimulus is provided via the electrode array to the auditory nerve, thereby causing a hearing percept.

Conductive hearing loss occurs when the normal mechanical pathways that provide sound to hair cells in the cochlea are impeded, for example, by damage to the ossicular chain or ear canal. Individuals suffering from conductive hearing loss may retain some form of residual hearing because the hair cells in the cochlea may remain undamaged.

Individuals suffering from conductive hearing loss typically receive an acoustic hearing aid. Hearing aids rely on principles of air conduction to transmit acoustic signals to the cochlea. In particular, a hearing aid typically uses a component positioned in the recipient's ear canal or on the outer ear to amplify a sound received by the outer ear of the recipient. This amplified sound reaches the cochlea causing motion of the perilymph and stimulation of the auditory nerve.

In contrast to hearing aids, certain types of hearing prostheses commonly referred to as bone conduction devices, convert a received sound into mechanical vibrations. The vibrations are transferred through the skull to the cochlea causing generation of nerve impulses, which result in the perception of the received sound. Bone conduction devices may be a suitable alternative for individuals who cannot derive sufficient benefit from acoustic hearing aids, cochlear implants, etc.

Some medical devices, such as transcutaneous bone conduction devices, have one or more components implanted in the recipient. Sometimes, the implanted components are secured to tissue of the recipient, sometimes they are attached to bone, and sometimes they are implanted (attached or otherwise) in a recess formed in the bone.

SUMMARY

In one aspect of the present invention, there is an implant comprising a compartment, wherein the implant is configured for secured implantation into a recess formed in a recipient's bone, and wherein the compartment is configured to removably retain a separate component such that the separate component is removable from the compartment without removing the implant from the bone.

In another aspect of the present invention, there is an implantable component, comprising a compartment and a vibratory element of a transcutaneous bone conduction device positioned in the compartment, wherein the implantable component is configured to be totally subcutaneously implanted in a recess formed in the recipient's bone.

In another aspect of the present invention, there is a medical procedure, comprising obtaining access to an implant totally subcutaneously implanted in a recipient, wherein at least a portion of at least a first component of the implant is located in a recess in bone and is osseointegrated to the bone, while the at least first component is located in the recess and is osseointegrated to the bone, detaching a second component from the first component, while the at least first component is located in the recess and is osseointegrated to the bone, removing the second component from within the recipient while the at least first component is located in the recess and is osseointegrated to the bone, and while the at least first component is located in the recess and is osseointegrated to the bone, reattaching the second component or attaching a third component to the first component such that the second component or the third component is subcutaneously implanted in the recipient.

In another aspect of the present invention, there is an implantable device, comprising a component configured to be removably retained in a compartment of an implant such that the component is removable from the compartment without moving the implant relative to an organ of a recipient proximate the implant.

BRIEF DESCRIPTION OF THE DRAWINGS

Embodiments of the present invention are described herein with reference to the attached drawing sheets in which:

FIG. 8 is a flowchart illustrating a procedure to remove an implanted module and replace the module or implant with a new module;

DETAILED DESCRIPTION

According to an exemplary embodiment, there is an implant comprising a substantially flat base with a circular periphery and a sidewall extending orthogonally therefrom. The combination of the base and the sidewall form a compartment with an opening opposite the base. The implant is configured for implantation into a recess formed in a recipient's skull and securement thereto via osseointegration. The implant is configured to removably receive in the compartment a separate implantable component, such as a module containing a vibrating actuator of a transcutaneous bone conduction device, such that the separate implantable component is removable from the implant without detaching the housing from the skull.

According to another exemplary embodiment, there is an implantable medical device including an implant which contains a functional component of the implantable medical device, such as a vibrating actuator of a transcutaneous bone conduction device. The implant comprises an enclosure in which the functional component is contained. The implant is configured for implantation into a recess formed in a recipient's bone and osseointegration thereto. In this exemplary embodiment, the implant is a monolithic structure that forms a hermetic enclosure that hermetically isolates the functional component from an external environment of the implant.

Figure 1:
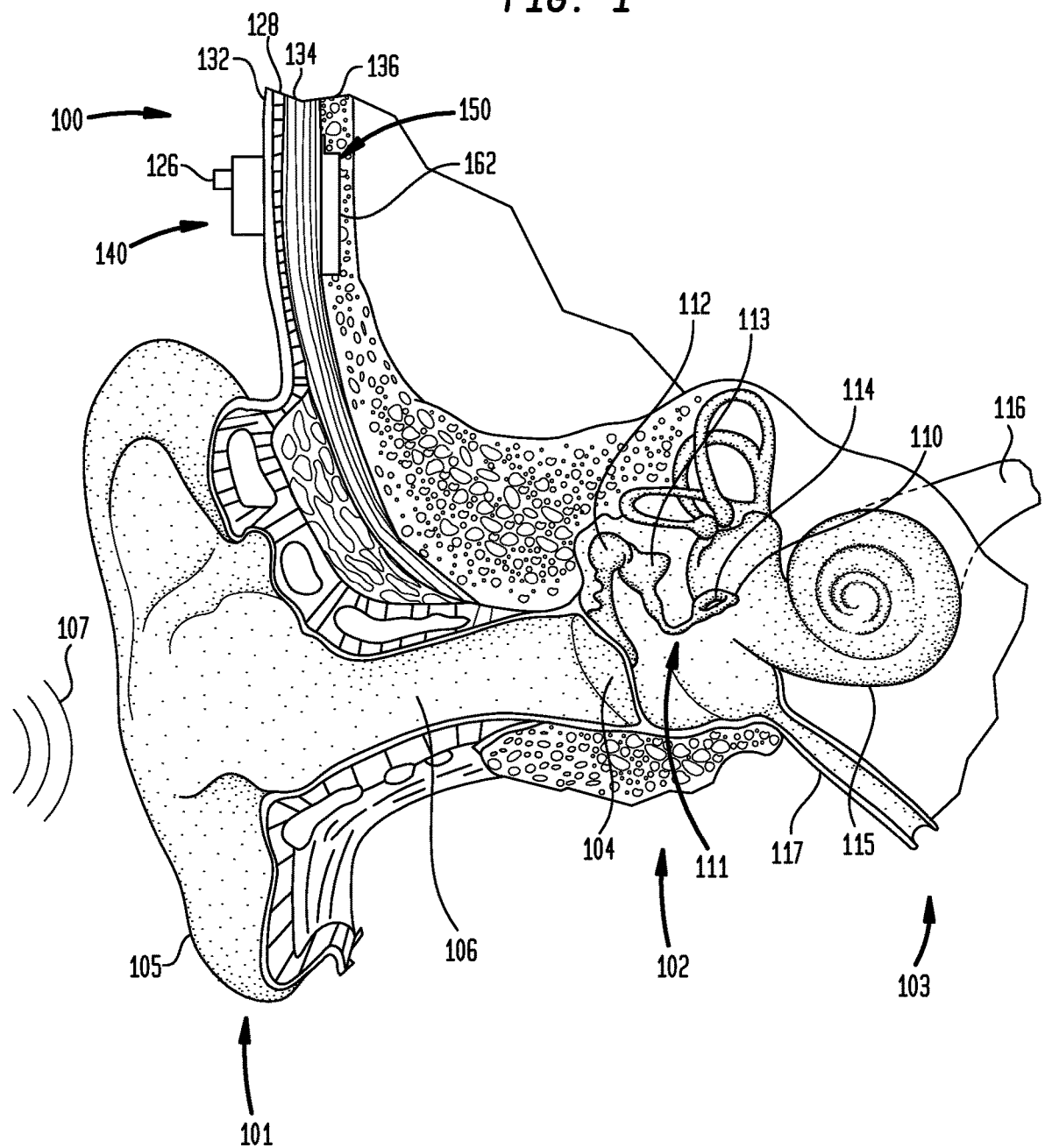
FIG. 1 is a perspective view of a transcutaneous bone conduction device in which embodiments of the present invention may be implemented.

FIG. 1 is a perspective view of a transcutaneous bone conduction device 100 in which embodiments of the present invention may be implemented. As shown, the recipient has an outer ear 101, a middle ear 102 and an inner ear 103. Elements of outer ear 101, middle ear 102 and inner ear 103 are described below, followed by a description of bone conduction device 100.

In a fully functional human hearing anatomy, outer ear 101 comprises an auricle 105 and an ear canal 106. A sound wave or acoustic pressure 107 is collected by auricle 105 and channeled into and through ear canal 106. Disposed across the distal end of ear canal 106 is a tympanic membrane 104 which vibrates in response to acoustic wave 107. This vibration is coupled to oval window or fenestra ovalis 110 through three bones of middle ear 102, collectively referred to as the ossicles 111 and comprising the malleus 112, the incus 113 and the stapes 114. The ossicles 111 of middle ear 102 serve to filter and amplify acoustic wave 107, causing oval window 110 to vibrate. Such vibration sets up waves of fluid motion within cochlea 139. Such fluid motion, in turn, activates hair cells (not shown) that line the inside of cochlea 139. Activation of the hair cells causes appropriate nerve impulses to be transferred through the spiral ganglion cells and auditory nerve 116 to the brain (not shown), where they are perceived as sound.

FIG. 1 also illustrates the positioning of bone conduction device 100 relative to outer ear 101, middle ear 102 and inner ear 103 of a recipient of device 100. As shown, bone conduction device 100 is positioned behind outer ear 101 of the recipient. It is noted that in other embodiments, the bone conduction device 100 may be located at other positions on the skull. Bone conduction device 100 comprises an external component 140 and implantable component 150. External component 150 is located beneath skin 132, and partially or fully below adipose tissue 128 and/or muscle tissue 128. The bone conduction device 100 includes a sound input element 126 to receive sound signals. Sound input element 126 may comprise, for example, a microphone, telecoil, etc. In an exemplary embodiment, sound input element 126 may be located, for example, on or in bone conduction device 100, on a cable or tube extending from bone conduction device 100, etc. Alternatively, sound input element 126 may be subcutaneously implanted in the recipient, or positioned in the recipient's ear. Sound input element 126 may also be a component that receives an electronic signal indicative of sound, such as, for example, from an external audio device. For example, sound input element 126 may receive a sound signal in the form of an electrical signal from an MP3 player electronically connected to sound input element 126.

Bone conduction device 100 comprises a sound processor (not shown), an actuator (also not shown) and/or various other operational components. In operation, sound input device 126 converts received sounds into electrical signals. These electrical signals are utilized by the sound processor to generate control signals that cause the actuator to vibrate. In other words, the actuator converts the electrical signals into mechanical vibrations for delivery to the recipient's skull.

In accordance with embodiments of the present invention, a fixation system 162 may be used to secure implantable component 150 to skull 136. As described below, fixation system 162 may include an implant at least partially embedded in the skull 136.

In one arrangement of FIG. 1, bone conduction device 100 is a passive transcutaneous bone conduction device. That is, no active components, such as the actuator, are implanted beneath the recipient's skin 132. In such an arrangement, the active actuator is located in external component 140, and implantable component 150 includes a movable component as will be discussed in greater detail below. The movable component of the implantable component 150 vibrates in response to vibration transmitted through the skin, mechanically and/or via a magnetic field, that are generated by an external magnetic plate.

In another arrangement of FIG. 1, bone conduction device 100 is an active transcutaneous bone conduction device where at least one active component, such as the actuator, is implanted beneath the recipient's skin 132 and is thus part of the implantable component 150. As described below, in such an arrangement, external component 140 may comprise a sound processor and transmitter, while implantable component 150 may comprise a signal receiver and/or various other electronic circuits/devices.

Figure 2A:
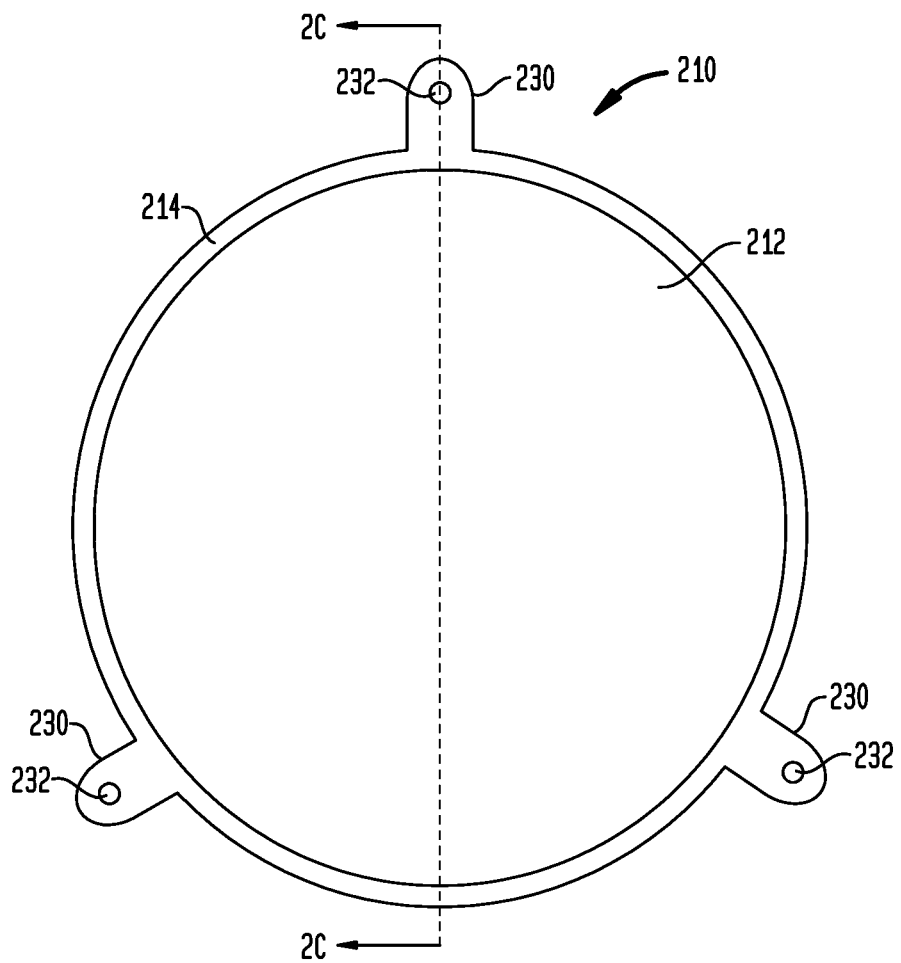
FIG. 2A is a top perspective view of an exemplary implant.
Figure 2B:
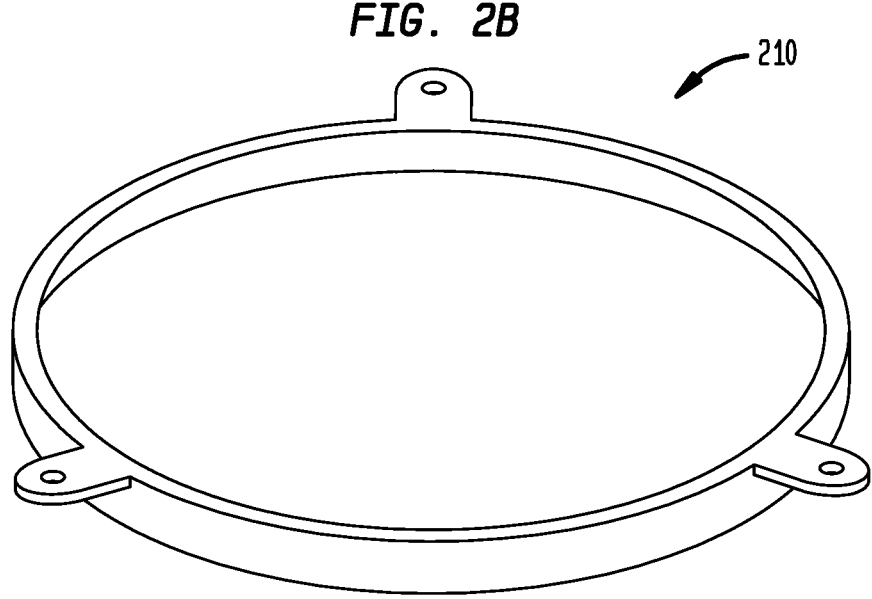
FIG. 2B is an isometric view of the exemplary implant of FIG. 2A.
Figure 2C:
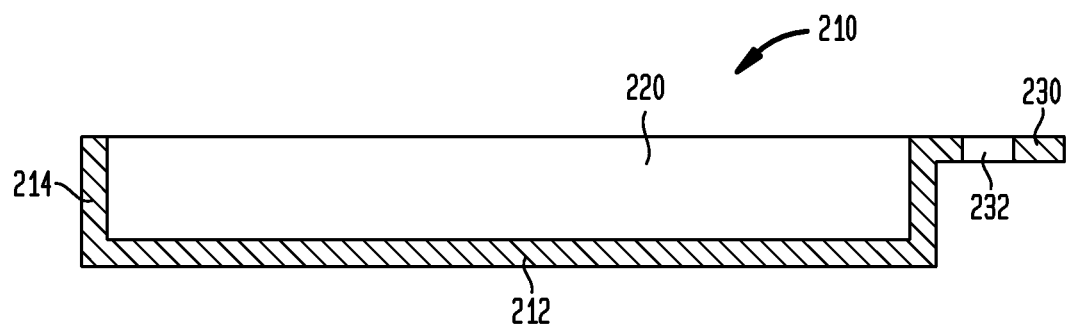
FIG. 2C is a side perspective view of the exemplary implant of FIG. 2A.
Figure 2D:
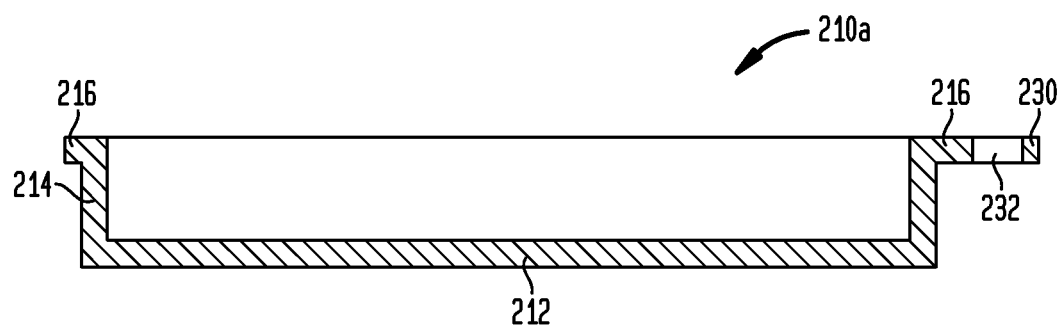
FIG. 2D is a side perspective view of an alternate exemplary implant.

FIGS. 2A, 2B and 2C depict an exemplary implant 210 usable in the fixation system 162 detailed above with implantable component 150. The implant 210 illustrated includes a base 212 and sidewall 214 extending orthogonally from the base 212. The base 212 and sidewall 214 of the housing 100 firm an open compartment 220. The compartment 220 is configured to house components of the implantable medical device 150 as will be described further below. The exterior portions of the sidewall 214 and/or the base 212 are configured to interact with a recess formed in the skull as will be described further below. Extending from the outer perimeter of sidewall 214 are three fixation arms 230 configured with respective through holes 232 through which a bone screw may be inserted for additional bone fixation capability, also as will be described further below. In some embodiments, a flange 216 extends about the perimeter of the sidewall 214 at the top of the sidewall 214, as may be seen by way of example in FIG. 2D, which depicts a derivative of implant 210 in the form of implant 210a. In embodiments that include fixation arm(s) 230, the fixation arms may have the same thickness as the flange 216, as depicted in FIG. 2D or may have a different thickness. In an exemplary embodiment, the bottom surface of the flange 216 lies substantially flush on the top of the skull.

It is noted that in some exemplary embodiments, there is no base 212 or a partial base 212. That is, there is an opening at the bottom of the implant 210. Alternatively or in addition to this, some or all of the base 212 may comprise a thin flexible diaphragm extending from sidewalk 214 and/or from an inner boundary of the partial base 212.

Figure 3:
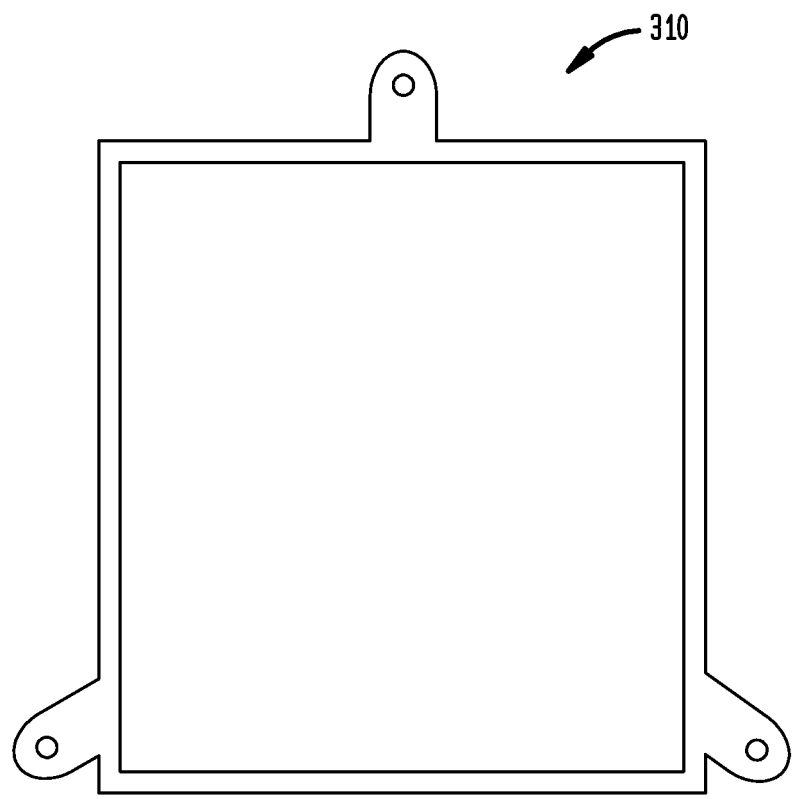
FIG. 3 is a top perspective view of an alternate exemplary implant.
Figure 4:
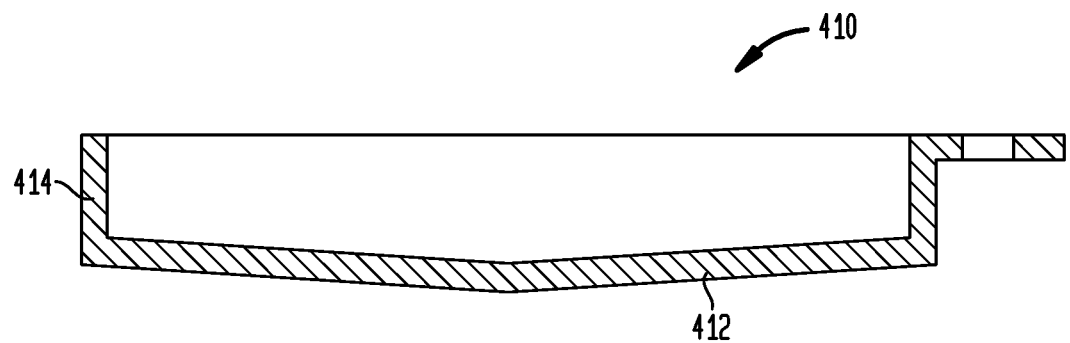
FIG. 4 is a side perspective view of an alternate exemplary implant.

As may be seen from FIGS. 2A-2D, the implant 210 may be in the form of a circular cylinder. More specifically, the implant 210 may have a circular cross-section on a plane normal to the longitudinal axis. In other embodiments, the implant may be in the form of another configuration, such as an implantable receiver housing 310 having a square cross-section on a plane normal to the longitudinal axis as may be seen in FIG. 3, etc. Also, while the embodiment depicted in FIGS. 2A-2C has a relatively flat base 212 that extends orthogonally from the sidewall 214, other embodiments include an implantable receiver housing 410 that has a base 412 that extends away from the sidewall 414 at an angle such as that seen in FIG. 4. Any configuration of the implant may be used providing it permits at least some embodiments to be practiced.

In an exemplary embodiment, the implant 210, 310 and/or 410 (hereinafter, unless otherwise specified, reference to one implant corresponds to the other implants and variations thereof) is made of titanium or other suitable metal or metal alloy. The implant 210 is a monolithic component which may be obtained via a casting method, metal/plastic stamping method, machining method, etc. In some embodiments the implant 210 is made of metal and/or a metal alloy, plastic (e.g., polyether ether ketone PEEK™), etc. Any suitable material that will permit embodiments to be practiced as detailed herein may be used in some embodiments. In other embodiments, the implant 210 is an assembly. For example, implant 210 may be a weldment where the base 212 and the sidewall 214 are welded together. Still further by example, the implant 210 may be a fitment where the base 212 and the sidewall 214 are screwed together (the implant 210 may have a seal or the like at the mating sections of the 212 and the sidewall 214 to obtain a hermetic seal at that location, as will be described more generally below). Any system or method of making the implant may be used, and the implant may take any form, providing it permits at least some embodiments to be practiced.

Figure 5A:
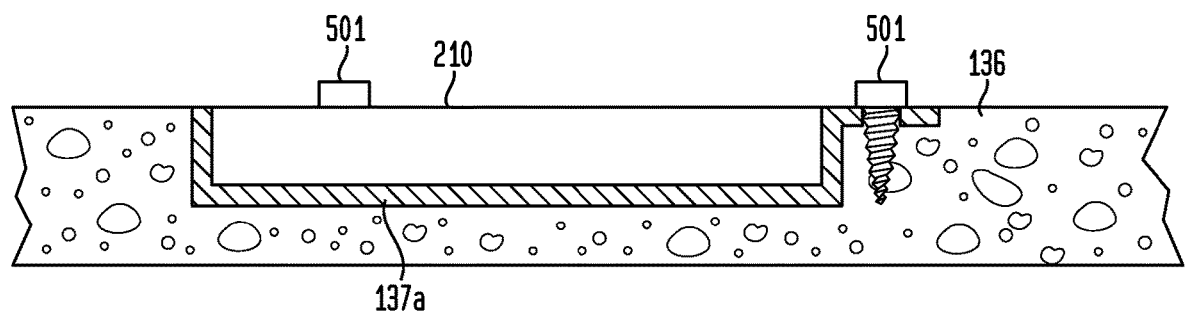
FIG. 5A is a perspective view of the exemplary implant of FIG. 2A implanted in the skull.

In an exemplary embodiment, at least some of the outer surfaces of base 212 and/or sidewall 214 form a bone interface region. In an exemplary embodiment where the implant 210 is fully implanted into the skull 136, as depicted by way of example in FIG. 5a, all of the outer surfaces of base 212 and all of the side surfaces of the sidewall 214 form a bone interface region, as may be seen. FIG. 5A also depicts the use of bone screws 501 which penetrate through holes 232 in arms 230, as will be discussed further below. In another exemplary embodiment where the implant 210 is partially implanted into the skull 136, as depicted by way of example in FIG. 5b, all of the outer surfaces of base 212 and a portion of the side surfaces of the sidewall 214 form a bone interface region, as may be seen.

Figure 5B:
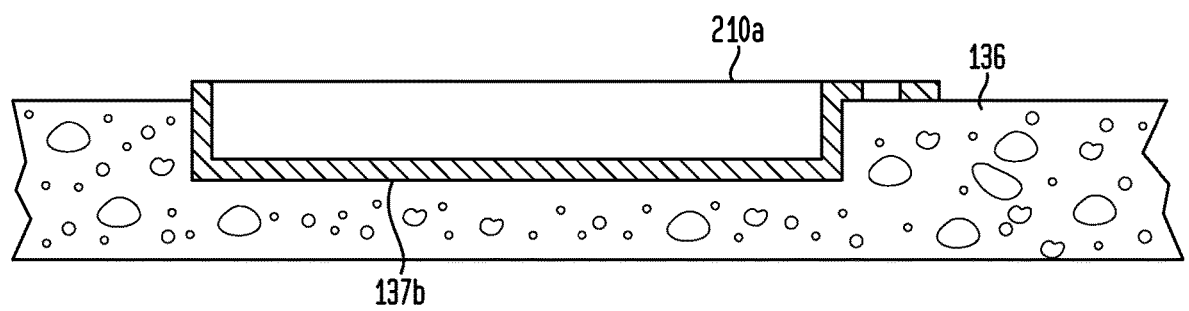
FIG. 5B is a perspective view of the exemplary implant of FIG. 2A implanted in the skull in a different manner than that of FIG. 5A.
Figure 6:
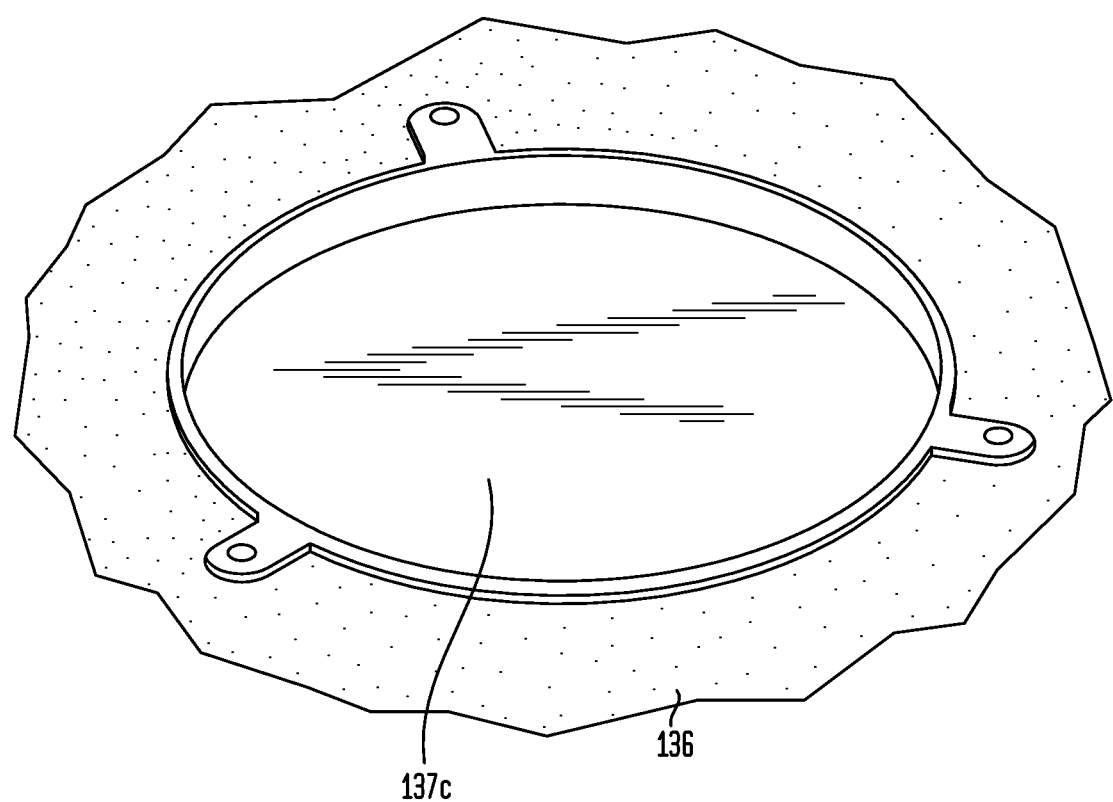
FIG. 6 is an isometric view of an exemplary recess within the skull.

As mentioned above, the implant 210 is configured to sit in a recess in the skull 136 as opposed to on the top of the skull. That is, some or all of the implant 210 extends below an extrapolated profile of the skull (i.e., where the surface of the skull would be/was prior to forming the recess in the skull). FIGS. 5A and 5B depict exemplary recesses 137a and 137b, respectively. As may be seen from FIG. 5A, the recess 137a includes a portion to receive fixation arms 230. However, in an alternate embodiment, where the implant 210 is partially implanted into the skull 136, such as shown in FIG. 5B, the receiver may not include a portion to receive fixation arms 230, at least in embodiments where the implant 210 is implanted to a depth such that the bottom of the fixation arms 230 remain above (including flush) with the outer surface of the skull 136. FIG. 6 depicts an isometric view of an exemplary implant 137a corresponding to, for example, implant 210a, fitted into an exemplary recess in skull 136. The exemplary recess includes a portion to receive fixation arms 230 and a portion to receive flange 216. In an exemplary embodiment, implant 210a is configured to be partially implanted into a recess such that a portion (approximately ½, ⅓, ⅔, ¾, ¼, etc.) of the thickness of the flange 216 in the longitudinal direction of the implant 210a extends above the outer surface of the skull 136.

In an exemplary embodiment, the implant 210 rests on/in the recess formed in the skull. The bone interface surface of the implant 210 is configured to osseointegrate with the bone with which it interfaces. In an exemplary embodiment, the bone interface surface has an osseointegration enhancing surface that may be textured, the texture improving osseointegration. Further, the bone interface surface may be coated with an osseointegration enhancing substance. In an exemplary embodiment, the bone interface surface has an anti-microbial (including anti-bacterial) that inhibits (including prevents) microbial growth and/or attachment thereon. Further, the bone interface surface may be coated with an anti-microbial substance that inhibits microbial growth and/or attachment thereon. In an exemplary embodiment, the portions of the implant 210 that make up the bone interface surface may be made of any material that has a known ability to integrate into surrounding bone tissue.

In an exemplary embodiment, the implant 210 is not fixed at essentially one central point to the skull, in contrast to, for example, a percutaneous bone conduction device that utilizes a bone fixture (also referred to as a bone screw) coupled to a skin penetrating abutment, and/or in contrast to an active or passive transcutaneous bone conduction device that utilizes a vibratory element linked to a bone fixture (bone screw) embedded in the skull. In an exemplary embodiment, the bone interface surface of, for example, the base 212 is expansive, and all or effectively all of the exterior surface of the base 212 may be osseointegrated to the skull. Alternatively or in addition to this, in some embodiments, all or substantially all of the bone interface surface of the sidewall 214 may also be osseointegrated to the skull to provide for substantially more mechanical support and stability relative to a fixation system utilizing a single central point. Further, the expansive bone interface surface of the base and/or the expansive bone interface surface of the sidewalk (which has a relatively large area owing to the fact that the area is linked to the radius of the base) provides for substantially much more mechanical support and stability relative to the fixation systems utilizing a single central point. In an exemplary embodiment, some or all of these features provide for an implant in which there is relatively little to no lever action, and at least substantially little to no lever action relative to the above-mentioned fixation systems utilizing a single central point (especially the percutaneous bone conduction device). In an exemplary embodiment, some or all of the exterior surface of the base 212 and/or some or all of the bone interface surfaces of the sidewalk 214 have a roughened part that enhances osseointegration relative to a non-roughened part. Alternatively or in addition to this, in an exemplary embodiment, some or all of the exterior surface of the base 212 and/or some or all of the bone interface surfaces of the sidewalks 214 have a coating of hydroxyapatite or other osseointegration-enhancing material that enhances osseointegration relative to a non-coated part.

As noted above, an exemplary embodiment utilizing the implants detailed herein corresponds to a transcutaneous bone conduction device. An embodiment includes stimulating and/or enhancing an osseointegration process via the use of a healing vibration mode whereby the transcutaneous bone conduction device is vibrated at a given frequency and cycle. In an exemplary embodiment, a vibrating element located in the implant may be used to stimulate/vibrate the bone in this healing vibration mode to improve osseointegration shorten a time period to obtain a level of osseointegration relative to the time period to obtain that level without the healing mode and/or improve the level of osseointegration in a given time period relative to that which would be obtained in that same time period without the healing mode) of the implant with the bone. Such improved osseointegration may improve hearing quality and/or allow a faster application of normal use of the hearing prosthesis of which the implant is apart. In an exemplary embodiment, a sensor located in the compartment may generate a feedback signal which may be detected by an external component regarding the quality of osseointegration at a given time.

In an exemplary embodiment, the implant 210 is configured to be held within a recess in the skull without positive mechanical retention. In such an exemplary embodiment, osseointegration of the bone interface surface with the skull holds the implant 210 within the recess. In such an exemplary embodiment, a slight interference fit may be relied on where the outer diameter of the sidewall 214 is slightly larger than the corresponding inner diameter of the recess. In an alternate embodiment, positive mechanical retention may be used to hold the implant 210 within the recess. By way of example, the exterior of the sidewall 214 and/or the base 230 may include male threads, grooves, etc., that interface with corresponding female threads, grooves, etc., to enhance securement of the implant 210 within the recess. In an exemplary embodiment, the implant 210 may be configured to snap-fit into the recess. By way of example, a male or female portion of the implant 210 may elastically deform to snap into a corresponding female or male portion of the skull 136 made by removing a portion of the skull 136. As will be further detailed below, fixation arms 230 with bone screws may be used to provide positive mechanical retention. In an alternate embodiment, the recess is provided with an offset relative to the dimensions of the implant. Any device, system or method that may be used to adhere the implant 210 in the recess in a manner sufficient to permit at least embodiments detailed herein and variations thereof to be practiced may be used in some embodiments.

In an exemplary embodiment, a healthcare provider (e.g., a surgeon or other type of medical doctor, a registered nurse practitioner, a surgeon technician, etc.) creates a predefined recess within the skull 136. In an exemplary embodiment, the healthcare provider identifies a type of implant receiver housing to be implanted (e.g., implant receiver housing 210, implant receiver housing 110a, etc.) and determines the geometry of the recess to be created. In this exemplary embodiment, implant receiver housing 210a is selected, and the healthcare provider creates a recess in the skull 136 corresponding to the recess associated with FIG. 6 and/or any of the other recesses detailed herein and variations thereof. This may be accomplished utilizing a customized bone/skull drill-tool which reproduces a given geometry of a recess that accepts a given geometry of the implant receiver housing 210, including recesses spaced at 120 degree intervals to receive at least a portion of the fixation arms 230. Other intervals may be used as well with evenly spaced intervals (for fewer or more arms) or otherwise. By way of example, this customized bone drill-tool permits the creation of a recess in a precise and repeatable way.

The healthcare provider performs this skull recession action until a clean dura surface in the skull is obtained for the compete footprint of the intended implant, at least with respect to those portions of the implant to be located below the natural surface of the skull. It is noted that in some embodiments, instead of drilling to the dura of the skull, the recess could be less deep. The dimensions of the recess are based on the dimensions and depth of the implant 210. For example, if the implant 210 has a height (as measured along the longitudinal axis) of 4.0 mm and the implant 210 is configured to be fully implanted in the skull 136, then the depth of the recess maybe 4.0 mm or more. Conversely, if the implant 210 has a height of 4.00 mm and the implant 210 is configured to be partially implanted in the skull 136, then the depth of the recess may be, by way of example, about 0.5 to about 2.0 mm. In an exemplary embodiment, such recess depths may be used in infant and/or child skulls which are typically not as thick as adult skulls.

The dimensions (e.g., shape, size) of the recess may be based on the dimensions of the implant 210. Any applicable dimensions of the recess and/or the implant 210 may be used in some embodiments so long as embodiments may be adequately practiced.

An alternate embodiment of the implant includes a central fixation device extending from the base of the implant. The central fixation device may be a screw that screws into a bone fixture located in the skull. As its name implies, the central fixation device may be located approximately at the center of the implant, while in other embodiments, it may be located away from the center of the implant. It is noted that in embodiments utilizing a central fixation device, the bone fixture may be implanted in a prior procedure to that of the implantation of the implant so as to provide a sufficient amount of time for the skull to heal from the first procedure and/or for the bone fixture to osseointegrate with the skull.

As noted above, the implant 210 includes a compartment 220 that is open on the side facing away from the skull 136. In an exemplary embodiment, the compartment 220 is configured to removably receive and removably retain a modular component of the implantable component in the compartment 220. An exemplary embodiment of a module 750 of which the implant 210a is configured to receive will be discussed in greater detail below. However, discussion will now be centered on exemplary retention mechanisms used with the implant 210a to removably retainably receive the module 750 therein and features of the module 750 which are used to insert and/or remove the module from the implant. By removably retainably receive, it is meant that the module 750 may be removed at least without having to structurally damage the implanted implant 210 or its securement to the skull. In this regard, module 750 may correspond to a component configured to be removably retained in compartment 220 of implant 210a such that the component is removable from the compartment 220 without moving the implant 210a, including relative to bone 136 (or another organ)/removing the implant from the bone 136 (or another organ) of a recipient proximate implant 210a.

Figure 7A:
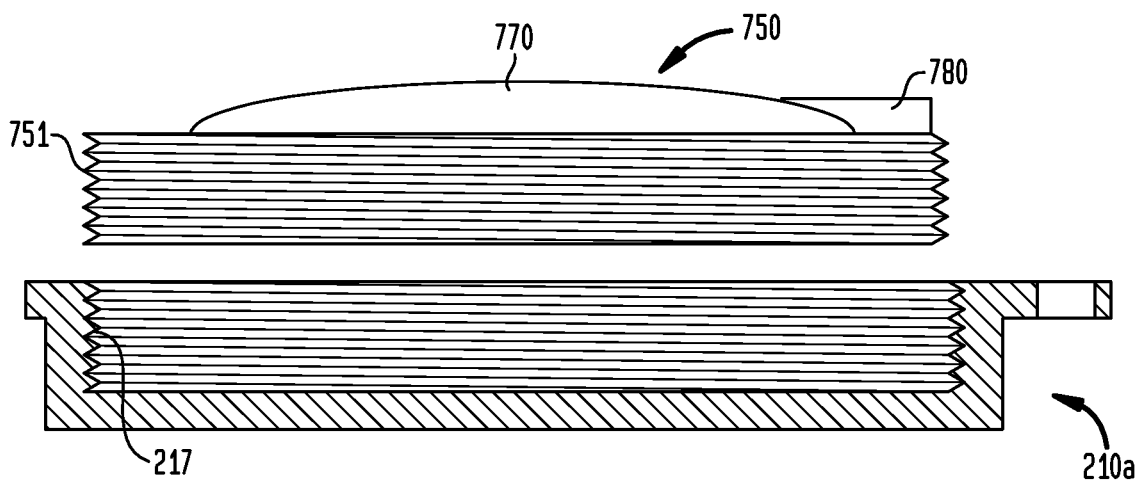
FIG. 7A is a side perspective view of an exemplary module configured to interface with the alternate exemplary implant of FIG. 2D.
Figure 7B:
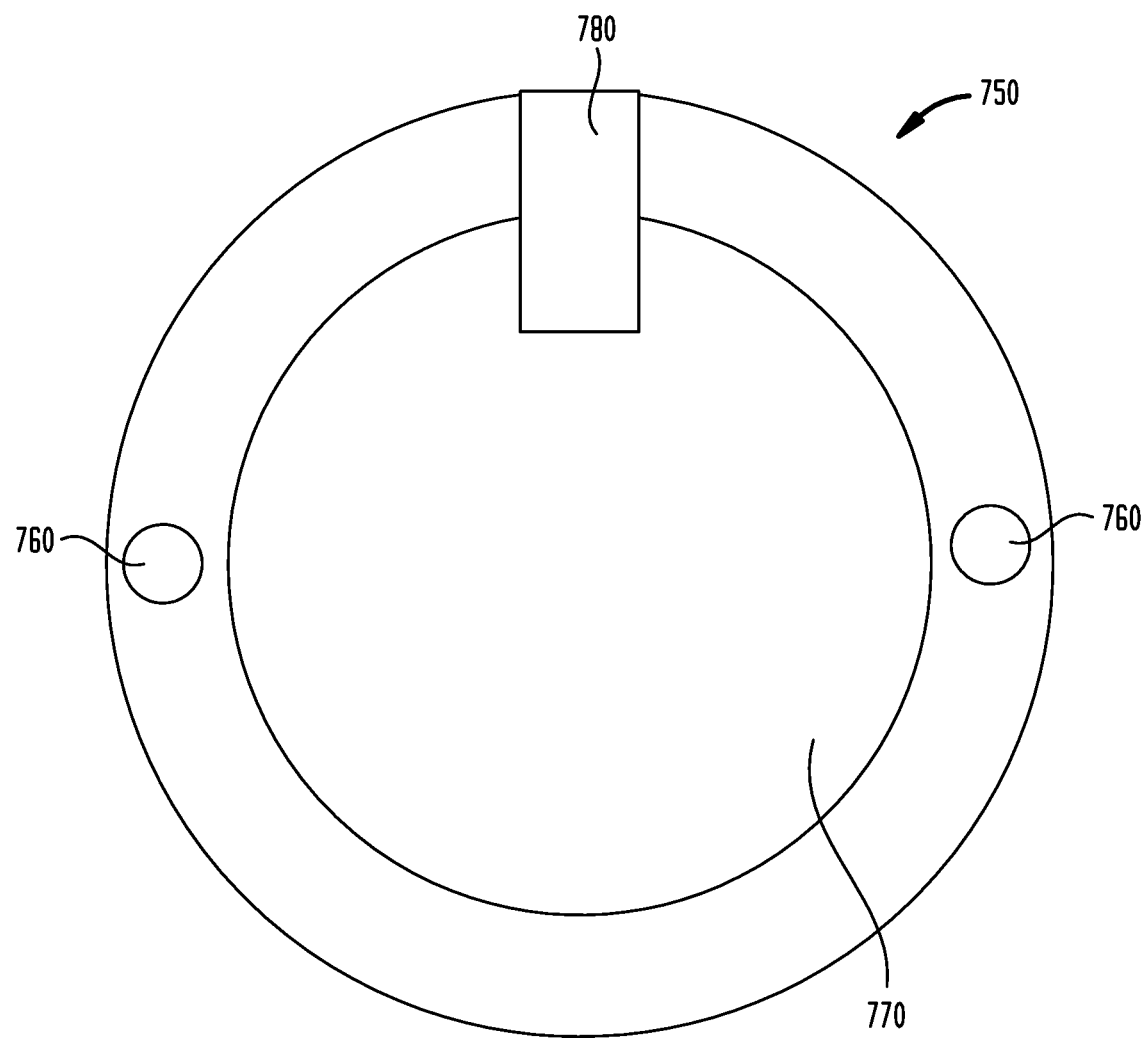
FIG. 7B is a top view of the exemplary module of FIG. 7A.

Referring to FIG. 7A, a side-view of the exemplary module 750 is depicted above an exemplary implant (in this example, implant 210a). FIG. 7B depicts a top view of the exemplary module 750 (without reference to an implant), The implant 210a includes an internal fixture mechanism that permits the module 750 (or other implantable components placed in the compartment 220) to connect securely to the implant 210a. The internal fixture mechanism may be a locking mechanism or the like that secures the components to the implant. The internal fixture mechanism may be located on the sidewall 214 and/or on the base 212. The internal fixture mechanism may comprise screw threads. For example, the implant 210a may include female threads 217 located on sidewall 214. Threads 217 interface/interact with respective male threads 751 located on the perimeter of module 750, thereby removably retaining the module 750 in the compartment 220. Accordingly, module 750 may be screwed into compartment 220 of implant 210a. Module 750 includes two depressions 760 located on the top surface thereof, although more or fewer depressions may be used in other embodiments. These depressions permit a healthcare professional to more easily transfer removal and/or installation torque from his or her fingers to the module 750. In an exemplary embodiment, these depressions or other depressions are configured to accept prongs of a specialized wrench to fit therein, thereby permitting removal and/or installation torque to be more easily transferred to the module 750. In an alternate embodiment, studs and/or prongs on module 750 may be used in lieu of or in addition to depressions 760 to apply installation/removal torque to the module 750. It is noted that in such an exemplary embodiment, the implant 210a is configured to be attached to the skull 136 in a manner that permits the installation and/or removal torques to be applied to the module 750 without dislodging the implant 210a from the skull. Accordingly, in an exemplary embodiment, module 750 includes a tool interface portion (depressions 760, studs, etc.) configured to interact with and react to at least one of force (which may be applied in an embodiment where the module 750 snap fits into compartment 220, discussed in greater detail below) or torque applied to the module 750, where the least one of the force or the torque corresponds to a force or torque sufficient to remove the module 750 from the compartment 220 after the module 750 has been removably retained therein. Module 750 further includes a dome 770. As will be described below, dome 770 or a comparable arched or partially arched structure is configured to provide protection from an external impact to the module 750.

In an exemplary embodiment, instead of the aforementioned male-female thread arrangement, a snap-fit arrangement, press-fit arrangement and/or an interference fit arrangement is used to couple module 750 to implant 210a. In this regard, the compartment 220 may correspond to a female part of a snap coupling between the module 750 and the implant 210a. In an exemplary embodiment, instead of the aforementioned male-female thread arrangement, a bayonet fitting arrangement is used to couple module 750 to implant 210a. Any device, system or method that will permit module 750 to be attached to implant 210a that permits at least some embodiments detailed herein and variations thereof to be practiced may be utilized in some embodiments. In an exemplary embodiment, the interior of the compartment 220 is in the form of a conical shape (extending inward with distance from the base 212. This may enhance a snap-fit arrangement, press-fit arrangement or interference fit arrangement used to couple module 750 to implant 210. In an exemplary embodiment, the fit between the two components may be tightened with a screw arrangement or the like.

Figure 7C:
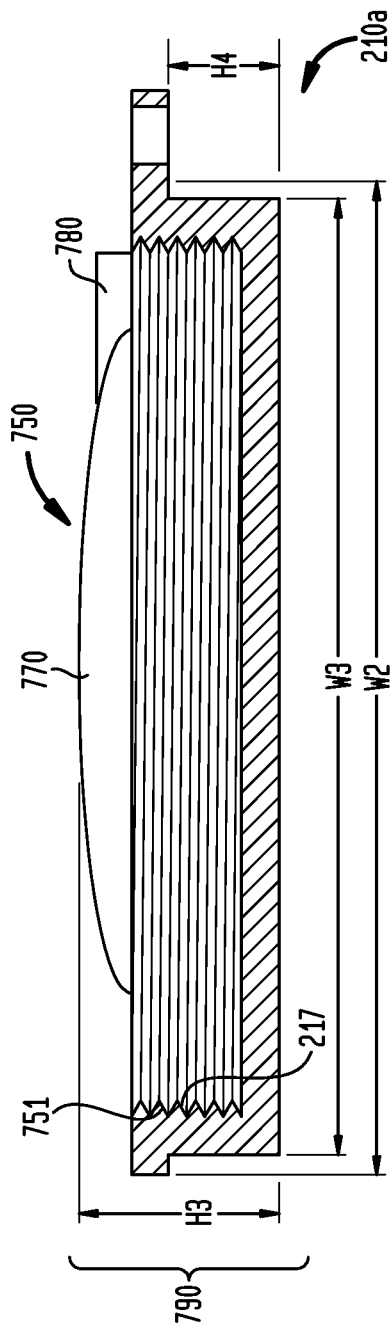
FIG. 7C is a side perspective view of the exemplary module of FIG. 7A received in the implant of FIG. 7A.

In some embodiments, the module 750 is dimensioned such that it fills all of the compartment 220, as may be seen in FIG. 7C, which depicts module 750 fully inserted into compartment 220, forming assembly 790. That is, the module 750 is dimensioned such that upon being fully seated on the base 212, all external surfaces of the module 750 are located at least flush with the top surface of the implant 210a. FIGS. 7A and 7B depict such exemplary embodiments. In alternate embodiments, the module 750 is dimensioned such that it fills only a portion of compartment 220. In an exemplary embodiment, if module 750 is fully seated on the base 212, at least some external surfaces of the module 750 facing away from the skull 136 are located below the top surface of the implant 210a. In some embodiments, the implant 210a is configured to leave a space between the bottom of the module 750 and the base 212.

In an exemplary embodiment, the overall height H3 of an exemplary assembly 790 formed when module 750 is fully inserted into compartment 220 of implant 210a, is about 6 mm, about 6.5 mm, about 7 mm, about 7.5 mm, about 8 mm, about 8.5 mm or about 9 mm or more or less, and/or may have a dimension falling between the just recited dimensions in any of about 0.1 mm increments. Of the overall height H3, about 2.5 mm, about 3.0 mm, about 3.5 mm, about 4.0 mm, about 4.5 mm, about 5.0 mm, about 5.5 mm or about 6 mm corresponds to H4, the height of the implant from the bottom of the implant to the bottom surface of flange 216 or the bottom surface of fixation arms 230, with the remainder corresponding to the height from the bottom surface of the flange 216 or the bottom surface of fixation arms 230 to the top of module 750. In some embodiments, assembly 790 has a width W2 or width W3 of about 20 mm, about 21 mm, about 22 mm, about 23 mm, about 24 mm, about 25 mm, about 26 mm, about 27 mm, about 28 mm, about 29 mm or about 30 mm, or more or less, and/or may have a dimension falling between the just recited dimensions in any of about 0.1 mm increments. Width W2 is measured from the outer circumference of flange 216, while width W3 is measured from the outer circumference of sidewalk 214.

The implant 210a is configured to form a hermetic seal with the module 750. In an exemplary embodiment, the implant 210a includes a seal, such as an O-ring seal, extending about the inner periphery of the compartment 220 that interfaces with the module 750 to prevent or at least effectively prevent the ingress of matter from outside the implantable component 150 formed by the implant 210a and the module 750 into any space between the module 750 and the implant 210a. In an alternative embodiment, the implant 210a includes a surface configuration that interacts with a seal located about the outer periphery of the module 750 to form a hermetic seal at that location. Surfaces of the implant 210a may include a chamfer feature that improves the sealing capability of the implantable component. Alternatively or in addition to this, the module 750 may include a chamfer feature, and may be configured to mate with the chamfer of the receiver housing 210a, In an exemplary embodiment, at least a portion of the implant 210a has a deformation zone located at, for example, the top interior circumference of the implant 210a (opposite the arms 230) that creates a tighter hermetic seal between the implant 210a and the module relative to the implant 210a not having the deformation zone.

In an exemplary embodiment, an anti-microbial surface or chemical coating may be located on one or more or all of the mating surfaces of the implant 210a and/or the module 750.

In an alternate embodiment, implant 210a is configured to removably receive a removable lid. In such an exemplary embodiment, an implantable component may be placed in the compartment 220 of implant 210a and a lid may be placed over the opening of compartment 220. Male threads may be included with the lid that interface with female threads 217 of implant 210a. Alternatively or in addition to this, the implant 210a may be configured to receive a mating portion of the lid at the top surface of the sidewall 214 and/or flange 216 (e.g., via a male portion having male or female threads that is received by a female portion of the sidewall 214 had has, respectively, female or male threads, etc.) The implant 210a is configured to form a hermetic seal at at least a portion of the interface of the removable lid and the implant 210a. In such an embodiment, the implantable component placed in the compartment 220 is shielded from the external environment of the implant 210a via the body of the implant 210a and the lid.

The removable lid can function as a protective cover for the implantable component placed in the compartment 220. Indeed, in some embodiments, the removable lid may also function as a protective cover for the implant 210a. In an exemplary embodiment, the removable lid may extend over the entire outer periphery of the implant 210a or at least the non-fixation arm periphery (the general periphery) of the implant 210a. The removable lid may have any dimension, size or shape that will permit embodiments to be practiced and variations thereof. As will be further detailed below, as with the module 750, the removable lid may have a dome shaped exterior that may provide enhanced resistance against external forces. In an exemplary embodiment, the domed shaped exterior is an epoxy-filled low-profile cover configured to divert substantially all (including all) impact forces to the circumference of the implant, as will be described in greater detail below.

Thus, the implantable component placed in the compartment 220 may not necessarily be hermetically sealed and/or may not necessarily be hardened to absorb the shock of an impact to the skin above the implant 210a s will be discussed below) because of the hermetic seal between the lid and the implant 210a and because the lid may be hardened and/or configured to diffuse the shock of impact. In an exemplary embodiment, the lid and module 750 are used together. The module 750 may be fully seated in the compartment 220, thus permitting a sufficient amount of female screw threads 217 to be exposed such that male threads of the lid may also interface with the female threads 217.

As mentioned above, in an exemplary embodiment, the module 750 or other components in the compartment 220 of the implant 210 may be accessed subsequent to implantation. In an exemplary embodiment, this may entail relatively minimal surgery. In an exemplary embodiment, this feature results from the fact that the module 750 and/or the removable lid are removable without removing the implant 210 from the skull 136 and/or moving the implant 210 relative to the skull 136. In an exemplary embodiment, a healthcare professional may repair, maintain and/or replace the module 750 and/or components in the compartment 220 without explanting the osseointegrated implant 210. In some embodiments where the implantable component 150 is implanted in a bone adjacent to the skin, such access may be attained with minimal surgery.

An exemplary embodiment entailing the implantation of a module 750 into an exemplary implant will now be described in the context of removing a previously implanted module 750 from the implant and either re-installing the previously implanted module 750 or installing a new module 750 in the implant. In an exemplary embodiment, the module 750 may be any module as detailed herein and variations thereof. In an exemplary embodiment, the implant may be any implant as detailed herein and variations thereof.

With reference to the procedure 800 represented in the flowchart of FIG. 8, at step 810, a health care professional obtains access to an implantable component 150. This may entail making an incision in the skin of the recipient to access implantable component 150. Implantable component 150 includes an implant according to an exemplary embodiment that has been implanted 5, 10, 15, 20 or more years previously. A module 750 which has been in the recipient for 2, 5, 10, 15, 20 or more years is located in the compartment of the implant.

At step 820, a healthcare professional removes the module 750 from the implanted implant and thus from the recipient.

At step 830, which is an optional step, the recipient's head is subjected to an MRI procedure. Because the module 750 has been removed from the recipient, the size and/or quantity of artifacts in the resulting MRI images is reduced. Further, any deleterious effects of the MRI procedure that might be induced by the presence of the module 750 are reduced and/or eliminated due to the absence of the module 750. An exemplary embodiment includes a module that contains a magnetic material (e.g., permanent magnet).

At step 840, upon a decision to reinstall the module removed from the recipient (such decision may or may not be part of the exemplary method 800), that module is reinstalled into the implant implanted in the recipient. Such reinstallation may be executed by executing the actions executed in the removal procedure of step 820 in reverse.

If a decision has been made to install a new module (such decision may or may not be part of the exemplary method 800), a new module having previously been obtained (again, which may or may not be part of the exemplary method 800), step 840 is skipped and step 850 is executed to install the new module into the implant implanted in the recipient. Such installation may be executed by executing the actions executed in the removal procedure of step 820 in reverse.

It is noted that if the module is to be reinstalled, step 850 may not be executed. It is further noted that in an embodiment, this permits controlled refitting of the implantable device 150 in that an upgraded implantable device 150 may be relatively easily obtained because the upgradable component is relatively easily removed from the recipient (e.g., because it is not osseointegrated to the skull). Moreover, some exemplary embodiments permit the new implant to be implanted at the exact same spot in the recipient, thus permitting an implant at the exact same location where the recipient became accustomed to having an implant. Further, no wait time is needed for osseointegration of the new component, as the interface between the new component and the skull remains the implant, which may be substantially fully osseointegrated to the skull.

As noted above, some embodiments of the implant include a flange 216, such as that depicted in FIG. 2D with respect to implant 210a. In an exemplary embodiment, the flange 216 facilitates osseointegration of the implant to the skull. As may be seen in FIG. 2D, the flange 216 extends from the perimeter of the sidewall 214. The flange 216 may conform to the skull surface or lay on a more shallow recess of the skull, such as the portion of the recess depicted in FIG. 6. That is, the flange 216 may rest on a portion of the skull where an additional recession is formed that conforms with the shape and diameter of the flange 216 to improve the interface with the skull. The shape, dimensions or size of the flange 216 may vary depending on the particular application for which the implant 210a is intended. An exemplary embodiment of the flange 216 includes a planar bottom surface configured to rest against the skull. The flange 216 may be configured to rest on the hard cortical top layer of the skull when the implant 210a is secured within the recess. The flange 216 may be an extension of the implant 210a and may be made of the same material as some or all of the other components of the implant. In some embodiments, the implant 210a is a monolithic component including the flange 216. In other embodiments, the flange 216 is a separate component from that of the rest of the implant 210a. In an exemplary embodiment, the flange 216 may be removably attached to the other portions of the implant 210a. The flange 216 may be formed such that it is relatively rigid while also being elastically and/or plastically malleable to conform to the corresponding portions of the skull to which/in which it is received. The flange 216 may be configured with varying thicknesses for different implants 210a.

As noted above, some embodiments of an implant include fixation arms 230. Fixation arms 230 may provide increased stability to the implant 210. Embodiments of an implant may include 1, 2, 3, 4, 5, 6 or more fixation arms 230. Note also that the fixation arms may not be uniform in design. As seen in FIGS. 2A-2D, the fixation arms 230 extend from the outer perimeter of sidewall 214 and/or the flange 216. As depicted in FIGS. 5A and 5B, the bottom portions of the fixation arms 230 are configured to rest securely on the skull 136.

Exemplary fixation arms 230 may have sufficient strength and stability to aid in securing the implant 210 within the recess of the skull. The fixation arms 230 may be secured to the skull surface (including surface of the portions of the recess formed to receive the fixation arms) by using bone screws, bone cement, etc. Any other fixation device, system or method may be used that will permit the fixation arms 230 to be secured to the skull in order for at least some embodiments to be practiced in accordance with the teachings herein and variations thereof. With regard to embodiments utilizing bone screws, the fixation arms 230 may have one or more pre-drilled openings or holes 232 configured to receive a bone screw or some other fixation device that interfaces with the holes 232. The fixation arms 230 may be a temporary fixation arm that is affixed to the outer perimeter of the flange 216 and/or the sidewall 214. In this regard, in an exemplary embodiment, the fixation aims 230 may be removed upon certain events, such as osseointegration between the other portions of the implant 210 and the skull. Thus, in some embodiments, the fixation arms 230 are removable/detachable. In an exemplary embodiment, the fixation arms may be bioabsorbable such that they dissolve (degrade) over time after implantation. Such an embodiment may utilize bone cement instead of screws to fix the fixation arms to the skull. It is noted that with respect to embodiments of the implant used with transcutaneous bone conduction devices, described further below, the screws may not transmit effectively any (including any at all) vibrations to the skull.

Figure 9:
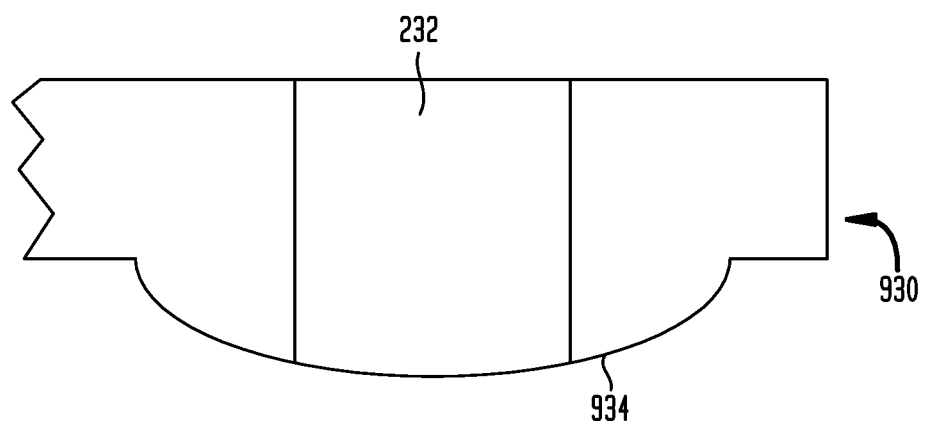
FIG. 9 is side perspective view of a rounded contact of a fixation arm.

In an exemplary embodiment, one or more of the fixation arms may have a rounded contact surface on the bottom-side of the fixation aim, as is depicted by fixation arm 930 in FIG. 9. The rounded bottom contact surface 934 may provide additional stable fixation and positioning of the implant 210. In an exemplary embodiment, the rounded bottom contact surfaces may be rounded "ball" contact surfaces. These surfaces may avoid rocking of the implant. The fixation arms may also be elastically and/or plastically deformable (upwards and/or downwards with respect to the longitudinal axis of the implant), and/or may have a slight upward orientation (away from the bottom of the implant).

In certain embodiments, designs of implants 210 may be standardized to have the same exterior dimensions and/or exterior dimensions corresponding to a limited number of different designs. In an exemplary embodiment, this may facilitate the standardization of the medical procedures used to form the recesses in the skull and the medical procedures used to implant the implants 210 in the recesses. Such a standardized designs and surgical procedures decreases the size of any gaps (including eliminating any gaps) between the bone and the bone interface surfaces (or, more accurately, the intended bone interface surfaces) of the implants 210. In an exemplary embodiment, this limits the potential for a conductive route for microbials to enter and/or a space for microbials to multiply to a level resulting in an infection that warrants medical attention.

The module 750 and/or compartment 220 (sealed with the removable lid) includes functional components of the implantable component 150. In an exemplary embodiment, this includes active components. In an exemplary embodiment, this may also or alternatively include passive functional components. One or more functional components may be located in the module 705 and/or compartment 220. The following exemplary embodiments are directed towards a hearing prosthesis in general, and a transcutaneous bone conduction device in particular. However, other embodiments include modules 750 and/or components contained in compartment 220 used in other types of prostheses. An exemplary embodiment of the implant 210 may be used with any type of prostheses providing that the teachings detailed herein and variations thereof may be practiced.

With reference to a transcutaneous bone conduction device, exemplary active components include, for example, an implantable actuator of an active transcutaneous bone conduction device. Active components further include an RF coil, a battery, an accelerometer, a microphone and a sound processor. Exemplary passive components include, for example, the implantable portion of a passive transcutaneous bone conduction device that vibrates or otherwise moves in response to vibrations transmitted through the skin of the recipient. An exemplary embodiment that includes a vibratory element contained in the module and configured to vibrate in response to a sound signal. In such an exemplary embodiment, the vibratory element may be that of a passive transcutaneous bone conduction device and/or that of an active transcutaneous bone conduction device. As will be understood from the exemplary embodiments of a functional component, general structural components (e.g., screws, bolts, joining elements, fixtures, conduits, etc.) are not functional components. Functional components are components that react to outside input and perform a function in response to that outside input. For example, in the case of a passive transcutaneous bone conduction device in which a vibratory element is located in module 750 (or in compartment 220), that vibratory element receives vibrations from the external component 140 and moves relative to skull to generate vibrations. In contrast, the implant 210 or a bone fixture, abutment and abutment screw of a percutaneous bone conduction device transmit vibrations from a vibratory element that moves, and thus they are structural, not functional, components.

Figure 10:
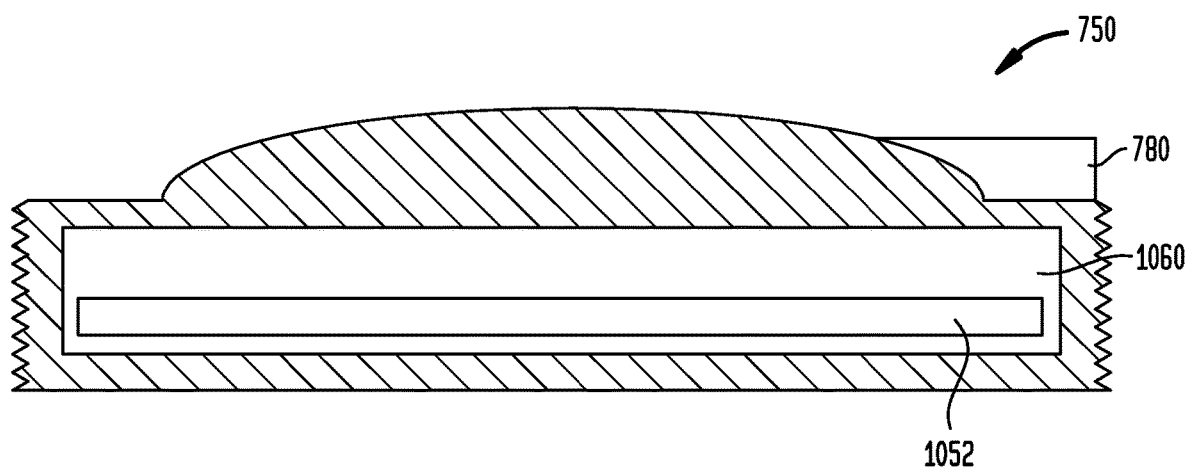
FIG. 10 is a side perspective view of a module having a vibratory element.

With respect to a vibratory element contained in module 750 and/or compartment 220, such as vibratory element 1052 as depicted in FIG. 10 (represented in black-box format, the vibratory element may be a passive plate that moves relative to the module 750 and/or compartment 220 in response to vibration or an active vibrating actuator that vibrates in response to received electrical input, as detailed below), the vibratory element is ultimately disposed within the implant 210 such that vibration stimulation to the skull occurs without any substantial (including any) losses. In this regard, the vibratory element (or any other vibration generating device) may generate vibrations that are transmitted through the implant 210 and into the skull, which are in turn transmitted by the skull and ultimately to the cochlea to provide a hearing precept. Osseointegration of the implant with the skull may, in some embodiments, permit optimal vibration conduction to the hard skull layer.

The direction of movement of the vibrating element may be axial and/or radial relative to the implant, thereby generating vibrations in the axial and/or radial direction relative to the implant.

As may be seen from the figures, an exemplary embodiment includes an implant configured to receive a module and/or having a compartment such that at least a portion of the functional component, and in some instances, the entire the functional component, is located below an extrapolated outer profile of the skull 136 (i.e., the profile of the skull that would be present if the recess had not been formed into the skull).

Referring back to FIG. 1, where implantable device 150 corresponds to a fixation system using an implant as detailed herein and variations thereof and a module 750 inserted in the compartment 220 of the implant, in an exemplary embodiment of a passive transcutaneous bone conduction device, a vibrating actuator is located in the external component 140. The vibrating actuator is located in housing of the external component 140, and is coupled to a plate. The plate may be in the form of a permanent magnet and/or in another form that generates and/or is reactive to a magnetic field, or otherwise permits the establishment of magnetic attraction between the external device 140 and the implantable component 150 sufficient to hold the external device 140 against the skin of the recipient.

In an exemplary embodiment, the vibrating actuator of the external component 140 is a device that converts electrical signals into vibration. In operation, sound input element 126 converts sound into electrical signals. Specifically, the passive transcutaneous bone conduction device provides these electrical signals to the vibrating actuator, or to a sound processor that processes the electrical signals, and then provides those processed signals to the vibrating actuator of the external component. The vibrating actuator converts the electrical signals (processed or unprocessed) into vibrations. Because vibrating actuator of the external component 140 is mechanically coupled to the plate of the external component 140, the vibrations are transferred from the vibrating actuator to the plate.

The module 750, which is part of the implantable component 150, includes an implanted plate 1052 (also referred to herein as an implanted plate assembly, although for the purposes of describing this specific feature, the implantable plate assembly may comprise only one component, but it also may comprise more than one component) is made of a ferromagnetic material that may be in the form of a permanent magnet, that generates and/or is reactive to a magnetic field, or otherwise permits the establishment of a magnetic attraction between the external device 140 and the implantable component 150 sufficient to hold the external device 140 against the skin of the recipient. Accordingly, vibrations produced by the vibrating actuator of the external device 140 are transferred from the plate of the external component 140 across the skin to plate assembly 1052. This may be accomplished as a result of mechanical conduction of the vibrations through the skin, resulting from the external device 140 being in direct contact with the skin and/or from the magnetic field between the two plates. These vibrations are transferred without penetrating the skin with a solid object such as an abutment as detailed herein with respect to a percutaneous bone conduction device.

The module 750 is substantially rigidly attached to the implant such that vibrations from the plate assembly 1052 may be transmitted from the module 750 to the implant and thus into the skull with substantially no loss.

Referring back to FIG. 1, where implantable device 150 corresponds to a fixation system using an implant as detailed herein and variations thereof and a module 750 inserted in the compartment 220 of the implant, in an exemplary embodiment of an active transcutaneous bone conduction device, vibrating element 1052 is a vibrating actuator 1052 that is located in the module 750. Specifically, a vibratory element 1052 in the form of vibrating actuator 1052 is located in a hermetically sealed housing 1060 of the module 750 (or, in the case of the implant utilizing a lid, in the hermetically sealed compartment 220).

It is noted that the enclosure 1060 and/or the compartment 220 may also be hermetically sealed in the case where the vibratory element is a plate assembly as detailed above with respect to the passive transcutaneous bone conduction device.

In an exemplary embodiment, much like the vibrating actuator of the external device 140 described above with respect to the passive transcutaneous bone conduction device, the vibrating actuator of the implantable device 150 is a device that converts electrical signals into vibration.

External component 140 may include a sound input element 126 that converts sound into electrical signals. Specifically, the active transcutaneous bone conduction device provides these electrical signals to the implanted vibrating actuator 1052, or to a sound processor (not shown) that processes the electrical signals, and then provides those processed signals to the implantable component 150 through the skin of the recipient via a magnetic inductance link. In this regard, a transmitter coil of the external component 140 transmits these signals to an implanted receiver coil located in the module 750 or compartment 220 or in another module or compartment associated with a separate implant (discussed in greater detail below) of the implantable component 150. Components in the module 750/compartment 220 (or other components of a separate implant), such as, for example, a signal generator or an implanted sound processor, then generate electrical signals to be delivered to vibrating actuator 1052 via electrical lead assembly. The vibrating actuator 1052 converts the electrical signals into vibrations.

The vibrating actuator 1052 may be mechanically coupled to the module 750 and/or the compartment 220. The module 750 substantially rigidly attached to the implant such that vibrations from the vibrating actuator 1052 may be transmitted from the module 750 to the implant and thus into the skull with substantially no loss.

The above embodiments have been described in terms of a implant into which a functional component may be relatively easily removed and installed without removing the implant from the skull. An exemplary embodiment as will now be detailed includes an implantable component 150 that utilizes embodiments of the implant detailed above and variations thereof as part of an implant that forms a permanent enclosure (as distinguished from the enclosure formed by, for example, the lid in combination with the implant detailed above). By "permanent," it is meant that the structural integrity of the implant must be substantially structurally degraded to access the interior of the enclosure. In some embodiments, the permanent enclosure forms a hermetic environment vis-à-vis the external environment of the implant. In other embodiments, the enclosure does not form a hermetic environment.

Figure 11:
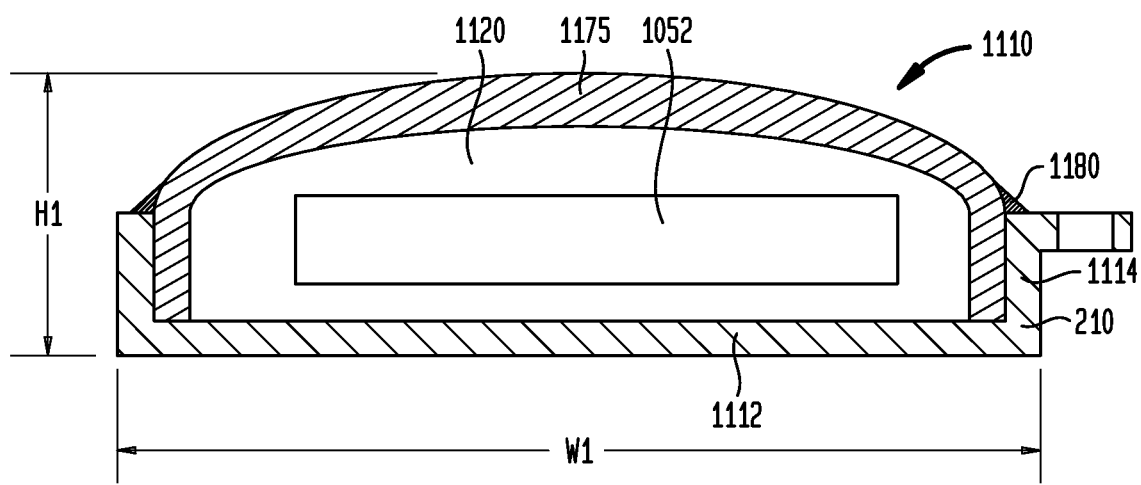
FIG. 11 is a side perspective view of an implant having a hood.

FIG. 11 depicts an exemplary implant 1110 according to such an embodiment, where implant 210 is mated with hood 1175 in a permanent manner (e.g., the hood 1175 is welded to implant 210 via weld 1180—this weld would need to be fractured or the material proximate the weld would need to be removed to remove the hood 1175 from the implant 210). The implant 1110 forms an enclosure 1120 in which a functional component 1052 is located, which may correspond to any of the functional components detailed herein and variations thereof, including a vibratory element. In an exemplary embodiment, implant 1110 includes the features and/or functionality of any of the embodiments of the implants, alone and/or in combination with a lid and/or module as detailed herein and variations thereof except that the enclosure (which may be considered to correspond to the compartment 220 for the purposes of this immediate discussion) is a permanent enclosure that permanently encloses the functional component 1052. Additional features of an implant will now be described. It is noted that unless otherwise specified, the features and/or functionality of any of the embodiments of the implants described herein and variations thereof are also present in the embodiments of the implants, alone or in combination with a lid and/or module as detailed herein and variations thereof.

Figure 12:
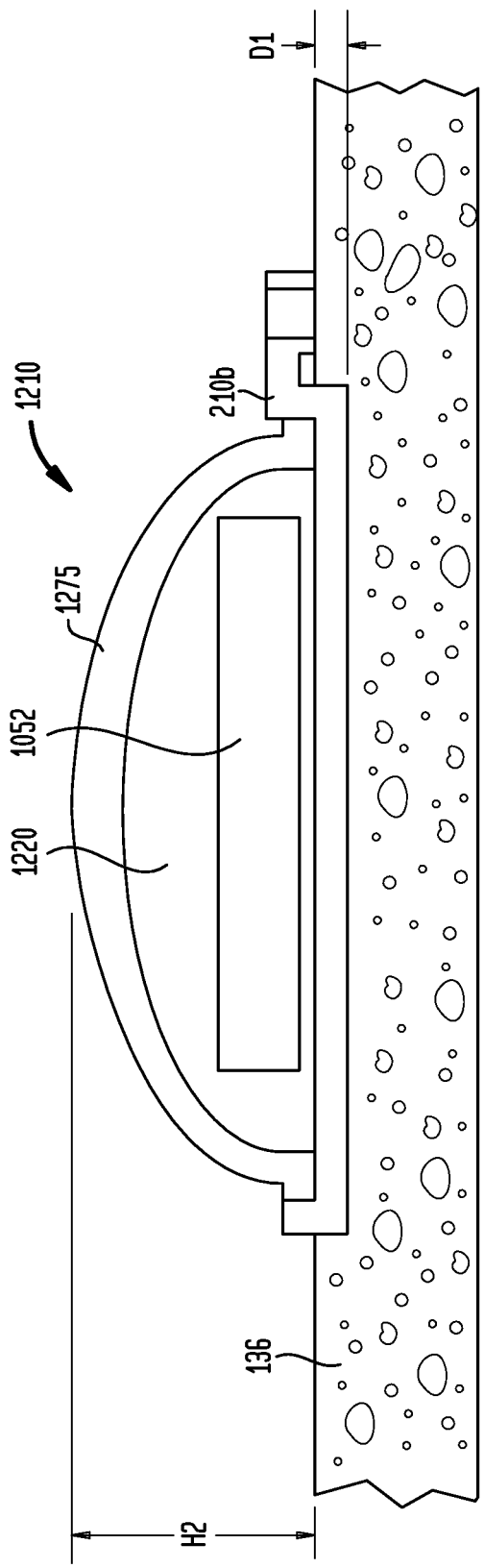
FIG. 12 is a side perspective view of an alternate embodiment of an implant having a hood.

In an exemplary embodiment, as may be seen in FIG. 11, the implant 1110 includes a hood 1175 that includes a domed portion that constantly curves along its span. With reference to FIG. 12 and hood 1275 (described further below), the outer surface of the dome may have a substantially constant radius, and thus may be in the form of a full or partial hemisphere. FIG. 12 depicts an arched hood 1275 in the form of a dome extending from a region proximate to the periphery of the implant 1210. Other convex (with respect to the enclosure 1120) shaped components may be used for the hood 1175. By way of example, partial dome may be used, where, for example, the hood arches for about ¼$^{th}$ the distance from its outer circumference, and then levels off to a flat surface for the remaining expanse across the enclosure 1120. Any geometric configuration of the hood may be used in some embodiments providing that embodiments as described herein and variations thereof may be practiced. In some embodiments, the hoods 1175 and 1275 and/or variations thereof may be used with some or no modification as lids for the implants detailed herein. Indeed, in an exemplary embodiment, hoods 1175 and 1275 are configured with male threads at the locations where the base of the hoods would interface with the implants. In an exemplary embodiment, the domed structure is reinforced with additional structure on the inside of the hoods, thus making a composite dome. Still further, the exterior of the hood may be in the form of a dome, white the interior of the hood may be substantially flat.

In an exemplary embodiment, the overall height H1 of an exemplary implant, such as implant 1120, is about 5 mm to about 6 mm (e.g., 5.5 mm, 6 mm, about 3.5 mm to about 7 mm, 2.5 mm, etc.). In an embodiment, the implants are configured to be inserted in a recess in the skull that extends top a depth of about 1 mm into the skull such that the implant extends about 0.5 to 1 mm into the skull, as may be seen in FIG. 12 with respect to D1. Accordingly, an exemplary embodiment may extend about 4.5 to about 5.5 mm above the surface of the skull, as may be seen in FIG. 12 with respect to H2. In some embodiments, the implant has a width (e.g., base diameter) of about 30 mm, as may be seen in FIG. 11 with respect to W1. The base portions of the implants of FIGS. 11 and 12 are depicted as having flat bases. However, bases such as the base used in FIG. 4 may be used. Along these lines, in an exemplary embodiment, the implants are configured to be inserted in a recess in the skull that extends to a depth of about 0.5 to 1 mm into the skull at the periphery of the recess and extends about 2 mm at about the center of the recess such that the implant extends about 0.5 to about 1 mm, about 3 to about 7 mm (or any range or specific value therein in 0.5 mm increments (e.g., it may extend to the dura of the skull)) into the skull at the periphery and about 2 mm at the center of the implant. In an exemplary embodiment, recesses extending 0.5 to 1 mm into the skull and/or about 2 mm into the skull may be used in pediatric subcutaneous applications. In an exemplary embodiment, the thickness of the hood is about 0.5 to about 1.0 mm (e.g., 0.8 mm). In an exemplary embodiment, with reference to FIG. 11, the implant 1110 includes a base 1112 located in a recess formed in a recipient's skull, the base 1112 having a diameter (W1) on a plane parallel to a bottom of the recess and/or parallel to the bottom of the base 1112 that is at least about twice, about three times, about four times and/or about five times the height H1 of the implant 1110 in a direction normal to the plane.

In view of the above, in an exemplary embodiment, there is an implantable medical device, comprising a functional component and a permanent enclosure in which the functional component is contained, wherein the implantable medical device is configured for implantation into a recess formed in a recipient's bone and osseointegrated thereto. In such an exemplary embodiment, the implantable medical device may be such that the interior of the enclosure is hermetically isolated from an external environment of the implantable medical device. Still further, in such an exemplary embodiment, the implantable medical device may be a monolithic implantable medical device. Alternatively or in addition to this, in such an exemplary embodiment, the implantable medical device may be substantially monolithic implantable medical device. Still further, in such an exemplary embodiment, the bone may be a bone of a skull, the functional component may be a vibratory element of a transcutaneous bone conduction device, the implantable medical device may be configured to be implanted no more than about 2 mm into the skull and the implantable medical device may be configured to transmit vibrations from the vibratory element to the implantable medical device and from at least portions of the implantable medical device implanted in the skull to the skull.

Alternatively or in addition to the exemplary embodiment(s) described in the preceding paragraph, the implantable medical device may include at least a partially arched hood covering the permanent enclosure configured to direct an impact load originating externally from the implantable medical device to a region at least proximate to a periphery of the implantable medical device. In such an exemplary embodiment, the at least partially arched hood may be a dome extending from a region at and/or proximate to the periphery of the implantable medical device.

As will be appreciated from a comparison between FIGS. 11 and 12, implant 1275 utilizes an implant that has sidewalk that are not as high as those of, for example, 210. Particularly, implant 210b of FIG. 12 is configured with sidewalk having a height of 1-2 mm. Accordingly, hood 1275 forms a substantial portion of the enclosure 1220. In an exemplary embodiment, the hoods detailed herein and variations thereof protect the functional components contained in the enclosure of the implant from some types of impact originating external to the recipient. Further, the hoods detailed herein and variations thereof, in some embodiments, are configured to reduce the risk of damage to the skin as a result of an impact originating external to the recipient. More particularly, some embodiments of the implant will be placed at a location on the body (e.g., skull) where there is relatively little distance between the apex of the hood and the surface of the skin (e.g., relatively little fat, muscle and a thin skin area). Moreover, some embodiments of the implant may be placed at a location on the body (e.g., skull) that is not shielded by other portions of the body. Thus, the implant may experience relatively high-load impacts during its implantation lifetime.

In view of the above, by placing the implant in a recess within the skull, it has a lower profile than if it were placed on the surface of the skull without a recess therein. Thus, the implant may have a height that is larger than one that is placed on the surface of the skull (because the recess in the skull absorbs some of that height). In an exemplary embodiment, this extra height permits the hood to extend from the periphery at a greater angle than it might otherwise extend and/or be thicker than it otherwise might be, thus permitting a geometry of the implantable hosing that better distributes the shock from an impact to the hood (and reducing the likelihood that the hood will collapse and/or the integrity of any hermetic environment of the enclosure is not lost). In an exemplary embodiment, the implant includes at least a partially arched hood covering the permanent enclosure configured to direct an impact load originating external from the implant to a region at and/or proximate to a periphery of the implant, such as, with respect to the embodiment of FIG. 11, the interior of the sidewall(s) 1114 and/or the outer periphery of the enclosure 1120 and/or the outer periphery of the base within the enclosure 1120 of the implant.

Alternatively or in addition to this, because of the lower profile, the implantable component does not extend above the surface of the skull to a height that it otherwise might extend, if at all, thus permitting the overall profile of the implant to be lower. In some exemplary embodiments, the geometries of the implant are such that the pinch hazard is reduced. That is, an exemplary embodiment includes a smooth and contoured hood extending to a maximum height above the skull such that it more evenly distributes pressure subjected to the skin from an impact. Put another way, the implant has a geometry that provides a reduced pinch hazard, thus limiting damage to soft tissue and recipient discomfort.

In an exemplary embodiment, the implant is configured with a geometry such that an impact force delivered to the hood is distributed to the periphery of the implant, and thus to the sidewalls and into the base of the implant, which rests flat or substantially flat in the surface of the recess of the skull. In an exemplary embodiment of this embodiment, the implant is thus more shock resistant than if the impact force was distributed to other portions of the implantable component.

In an exemplary embodiment, all or effectively all of the components of the implant are configured such that there are no "free hanging" housing ends. In this regard, the fixation arms may lie flat on bone surface (on the skull surface or recess surface). Such a configuration reduces (including eliminates) additional implant resonance frequencies in the audio spectrum which may deleteriously affect the audio performance of a transcutaneous bone conduction device.

In an exemplary embodiment, the implant has no joints or mating components on the exterior surface that are not fused together (e.g., via welding, sintering, etc.). Hereinafter, such an embodiment is referred to as a monolithic implant. However, in an alternate embodiment, there is an implant that has no joints or mating components on the exterior surface that are not fused together with the exception of an electrical lead port (discussed further below). Hereinafter, such an embodiment is referred to as a monolithic implant with electrical lead ports. In such an exemplary embodiment, the risk of infection by microbes may be reduced as compared to an implant with joints or mating components on the exterior surface that are not fused together. In an exemplary embodiment, the monolithic implant and/or the substantially monolithic implant has a relatively high reliability because there are no parts of the implant which may become loose over time.

In an exemplary embodiment, all functional components of the implantable component 150 are located in a single implant. In an alternate embodiment, all functional components except for a telecoil and/or a rechargeable battery are located in a single implant, and the telecoil and/or battery is located in a separate implant. In the same vein, in an exemplary embodiment, all functional components of the implantable component 150 are located in a single module located in a single implant. In an alternate embodiment, all functional components except for a telecoil and/or a rechargeable battery are located in a single module received in a single implant, and the telecoil and/or battery is located in a separate module received in a separate implant. Respective lead assemblies etc. the two implants and modules.

Figure 13:
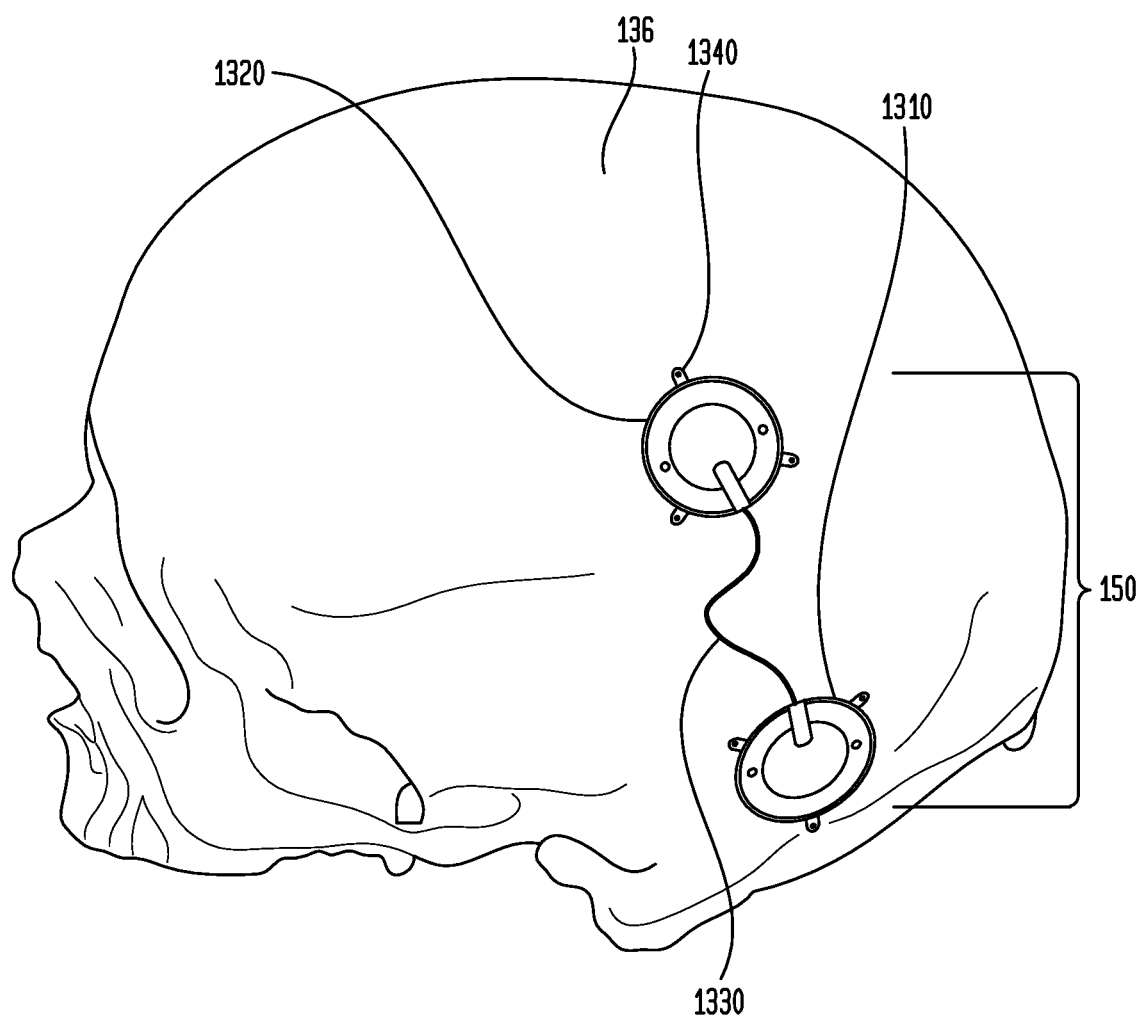
FIG. 13 is perspective view of an implantable component in the form of an active transcutaneous bone conduction device.

FIG. 13 depicts an implantable component 150 in the form of an active transcutaneous bone conduction device. Implantable component 150 comprising two implants 210a and two modules 750 respectively received therein, respectively forming assembly 1310 and assembly 1320. The implants are received in the skull 136 as detailed herein. Each implant 210a includes three bone screws 1310 that extend through respective fixation arms and into the skull 136 as detailed herein. Assembly 1310 includes a vibrating actuator and a control unit. The vibrating actuator vibrates, and those vibrations are transmitted from the module 750 in which it is located to the implant 210a that receives that module and then to the skull 136 as detailed herein so as to provide vibrations to the cochlea (not shown) to impart a hearing precept. Assembly 1320 includes an RF telecoil and a rechargeable battery. The RF telecoil receives a transcutaneous RF signal and outputs an electrical signal to the assembly 1310 via lead assembly 1330 that extends between assemblies 1310 and 1320.

Lead assembly 1330 enters the respective modules 750 via lead port 780 (with reference to FIG. 10). Lead port 760 provides a shielded inlet for the lead assemblies and prevents the lead assembly from being pinched between portions of the implantable component 150. As may be seen, it is located on the top of the module 750. Lead port 760 may include a feedthrough that is hermetically sealed in the module 750. Thus, instead of entering the module 750, the lead assembly is connected to the feedthrough and the electrical signals are transferred from the lead assembly to the feedthrough and thus into the module 750 through the feedthrough.

In an exemplary embodiment, the lead port 760 is configured such that the lead enters the lead port at a location that permits the lead to remain on the skull until it reaches the assembly 1310 and/or 1320. In an alternate embodiment, the implant 210a and/or the module 750 is configured such that the lead may extend from the respective assembly below the surface of the skull. In an exemplary embodiment, a groove or the like is formed in the skull such that the lead assembly travels at least partially below the surface of the skull. This groove may extend from one assembly 1310 to the other assembly 1320, or may only partially extend from the respective assembly, thus providing a gradual transition from below the surface of the skull to above the surface of the skull. However, in an alternate embodiment, there is no lead assembly used in the implantable component 150. Instead, the assemblies 1310 and 1320 wirelessly communicate between one another.

In an exemplary embodiment, implant 210a may include a slit and/or a tube shaped or half-tube shaped opening at, for example, the top portion of the implant 210a through which a lead wire may exit the compartment 220.

An exemplary embodiment includes devices, systems and/or methods of forming the recesses in the skull or bones as disclosed herein and variations thereof. Still further, an exemplary embodiment includes the combination of any device disclosed herein and variations thereof with the recesses in the skull or bones as disclosed herein and variations thereof.

An exemplary embodiment utilizing two or more implants permits the functional components to be distributed across multiple implants thereby reducing the size of individual implants.

While various embodiments of the present invention have been described above, it should be understood that they have been presented by way of example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the following claims and their equivalents. All patents and publications discussed herein are incorporated in their entirety by reference thereto.

What is claimed is:

1. A medical procedure, comprising:
   obtaining access to an implant implanted in a recipient, wherein at least a portion of at least a first component of the implant is located in a recess in bone and is fixed to the bone;
   while the at least first component is located in the recess and is fixed to the bone, detaching a second component from the first component;
   while the at least first component is located in the recess and is fixed to the bone, removing the second component from within the recipient while the at least first component is located in the recess and is fixed to the bone; and
   while the at least first component is located in the recess and is fixed to the bone, reattaching the second component or attaching a third component to the first component such that the second component or the third component is attached to the recipient, wherein
   the first component is a housing;
   the second component is a component of a hearing prosthesis; and
   the third component is a replacement component of the hearing prosthesis.

2. The medical procedure of claim 1, wherein:
   the implant is implanted in a skull of the recipient; and
   the medical procedure further comprises:
      while the at least first component is located in the recess and is fixed to the bone, performing an MRI of the head of the recipient after the second component has been removed from within the recipient and prior to reattaching the second component or the third component to the first component.

3. The medical procedure of claim 1, wherein:
   the medical procedure converts the implant from an implant of a passive transcutaneous bone conduction device to a bone conduction device where a vibrator thereof is mechanically coupled to the first component, wherein the first component extends no more than 2.5 mm into the bone, wherein the bone is a skull of the recipient; and
   the first component has a maximum diameter of at least 20 mm.

4. The medical procedure of claim 1, wherein:
   the first component extends no more than 2.5 mm into the bone, wherein the bone is a skull of the recipient.

5. The medical procedure of claim 1, wherein:
   the first component extends no more than 5.0 mm into the bone, wherein the bone is a skull of the recipient.

6. The medical procedure of claim 1, wherein:
   the first component has a maximum diameter of between 20 mm to 30 mm, inclusive.

7. The medical procedure of claim 1, wherein prior to removing the second component, the second component is located in a cavity of the first component that is hermetically sealed.

8. The medical procedure of claim 1, wherein:
   the implant implanted in the recipient to which access is obtained is totally subcutaneously implanted in the recipient.

9. A medical procedure, comprising:
   obtaining access to an implant implanted in a recipient, wherein at least a portion of at least a first component of the implant is located in a recess in bone and is fixed to the bone;
   while the at least first component is located in the recess and is fixed to the bone, detaching a second component from the first component;
   while the at least first component is located in the recess and is fixed to the bone, removing the second component from within the recipient while the at least first component is located in the recess and is fixed to the bone; and
   while the at least first component is located in the recess and is fixed to the bone, reattaching the second component or attaching a third component to the first component such that the second component or the third component is attached to the recipient, wherein
   the first component is a housing;
   the second component is a permanent magnet;
   the third component includes a vibrating actuator; and the action of reattaching the second component or attaching the third component to the first component includes attaching at least a portion of the third component to the first component.

10. The medical procedure of claim 9, wherein:
the action of reattaching the second component or attaching the third component to the first component results in the second component or the third component being subcutaneously implanted in the recipient.

11. The medical procedure of claim 9, wherein:
the first component extends no more than 6.0 mm into the bone, wherein the bone is a skull of the recipient.

12. The medical procedure of claim 9, wherein removing the second component from within the recipient while the at least first component is located in the recess and is fixed to the bone includes removing the second component from the recess.

13. The medical procedure of claim 9, wherein:
there is bone underneath the entirety of the first component.

14. The medical procedure of claim 9, wherein:
the implant implanted in the recipient to which access is obtained is totally subcutaneously implanted in the recipient.

15. A medical procedure, comprising:
obtaining access to an implant implanted in a recipient, wherein at least a portion of at least a first component of the implant is located in a recess in bone and is fixed to the bone;
while the at least first component is located in the recess and is fixed to the bone, detaching a second component from the first component;
while the at least first component is located in the recess and is fixed to the bone, removing the second component from within the recipient while the at least first component is located in the recess and is fixed to the bone; and
while the at least first component is located in the recess and is fixed to the bone, reattaching the second component or attaching a third component to the first component such that the second component or the third component is attached to the recipient, wherein
the first component includes an open space established by a monolithic body, which space extends beneath an outer surface of the bone;
the second component is a permanent magnet; and
the third component includes a vibrator of a bone conduction device, wherein the third component includes a portion that is located within the space established by the monolithic body and a portion that extends out of the space established by the monolithic body.

16. The medical procedure of claim 15, wherein:
the first component is a housing; and
a functional component of the implant is attached to the second component.

17. The medical procedure of claim 15, wherein:
the third component is the vibrator of a bone conduction device.

18. The medical procedure of claim 15, wherein:
the third component is only the vibrator of a bone conduction device; and
the first component is a housing, and at least one of: (i) the first component is made of a metal or (ii) the first component is made of a polymer.

19. The medical procedure of claim 15, wherein:
the first component extends no more than 4.0 mm into the bone, wherein the bone is a skull of the recipient.

20. The medical procedure of claim 15, wherein:
the first component is a housing;
the second component is a component of a hearing prosthesis; and
the third component is a replacement component of the hearing prosthesis.

21. The medical procedure of claim 15, wherein:
the implant implanted in the recipient to which access is obtained is totally subcutaneously implanted in the recipient.

22. A medical procedure, comprising:
obtaining access to an implant totally subcutaneously implanted in a recipient, wherein at least a portion of at least a first component of the implant is located in a recess in bone and is fixed to the bone;
while the at least first component is located in the recess and is fixed to the bone, detaching a second component from the first component;
while the at least first component is located in the recess and is fixed to the bone, removing the second component from within the recipient while the at least first component is located in the recess and is fixed to the bone; and
while the at least first component is located in the recess and is fixed to the bone, reattaching the second component or attaching a third component to the first component such that the second component or the third component is attached to the recipient, wherein
the medical procedure converts the totally subcutaneous implant from an implant of a passive transcutaneous bone conduction device to a bone conduction device where a vibrator thereof is mechanically coupled to the first component.

23. The medical procedure of claim 22, wherein:
the first component extends no more than 3.5 mm into the bone, wherein the bone is a skull of the recipient.

24. The medical procedure of claim 22, wherein:
the first component has a maximum diameter of at least 30 mm and less than a maximum diameter of a skull of the recipient, the skull corresponding to the bone.

25. The medical procedure of claim 22, wherein reattaching the second component or attaching a third component to the first component such that the second component or the third component is attached to the recipient includes placing the second component or the third component into a cavity of the first component.

26. The medical procedure of claim 22, wherein the bone is a skull of the recipient, and wherein the recess is located behind an outer ear of the recipient and in front of a rear of the skull of the recipient.

* * * * *